(12) United States Patent
Falsafi et al.

(10) Patent No.: US 7,250,452 B2
(45) Date of Patent: *Jul. 31, 2007

(54) DENTAL COMPOSITIONS AND METHODS WITH ARYLSULFINATE SALTS

(75) Inventors: Afshin Falsafi, Woodbury, MN (US); Rajdeep S. Kalgutkar, St. Paul, MN (US); Joel D. Oxman, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 481 days.

This patent is subject to a terminal disclaimer.

(21) Appl. No.: 10/672,814

(22) Filed: Sep. 26, 2003

(65) Prior Publication Data
US 2005/0070627 A1    Mar. 31, 2005

(51) Int. Cl.
*A61K 6/083* (2006.01)
*C08K 5/41* (2006.01)
*A61C 5/00* (2006.01)

(52) U.S. Cl. .................... 523/115; 523/118; 524/167; 433/228.1

(58) Field of Classification Search ............... 523/115, 523/118; 524/167
See application file for complete search history.

(56) References Cited

U.S. PATENT DOCUMENTS

| | | |
|---|---|---|
| 3,556,794 A | 1/1971 | Margerum |
| 3,573,922 A | 4/1971 | Rust |
| 3,607,272 A | 9/1971 | Rust |
| 3,627,656 A | 12/1971 | Miller et al. |
| 3,642,487 A | 2/1972 | Rust |
| 3,708,296 A | 1/1973 | Schlesinger |
| 3,729,313 A | 4/1973 | Smith |
| 3,741,769 A | 6/1973 | Smith |
| 3,788,858 A | 1/1974 | Margerum |
| 3,808,006 A | 4/1974 | Smith |
| 4,052,244 A | 10/1977 | Skoultchi |
| 4,069,054 A | 1/1978 | Smith |
| 4,069,055 A | 1/1978 | Crivello |
| 4,182,035 A | 1/1980 | Yamauchi et al. |
| 4,216,288 A | 8/1980 | Crivello |
| 4,250,053 A | 2/1981 | Smith |
| 4,250,311 A | 2/1981 | Crivello |
| 4,257,915 A | 3/1981 | Eaton |
| 4,259,075 A | 3/1981 | Yamauchi et al. |
| 4,356,296 A | 10/1982 | Griffith et al. |
| 4,366,228 A | 12/1982 | Specht et al. |
| 4,394,403 A | 7/1983 | Smith |
| 4,455,147 A | 6/1984 | Lewis et al. |
| 4,499,251 A | 2/1985 | Omura et al. |
| 4,503,169 A | 3/1985 | Randklev |
| 4,537,940 A | 8/1985 | Omura et al. |
| 4,539,382 A | 9/1985 | Omura et al. |
| 4,642,126 A | 2/1987 | Zador et al. |
| 4,650,913 A | 3/1987 | Feiring |
| 4,652,274 A | 3/1987 | Boettcher et al. |
| 4,695,251 A | 9/1987 | Randklev |
| 4,755,620 A | 7/1988 | Iwamoto et al. |
| 4,859,572 A | 8/1989 | Farid et al. |
| 4,871,786 A | 10/1989 | Aasen et al. |
| 4,872,936 A | 10/1989 | Engelbrecht |
| 4,908,227 A | 3/1990 | Dougherty et al. |
| 4,959,297 A | 9/1990 | Palazzotto |
| 4,966,934 A | 10/1990 | Huang et al. |
| 4,971,892 A | 11/1990 | Ali et al. |
| 4,983,644 A | 1/1991 | Mukai et al. |
| 5,076,844 A | 12/1991 | Fock et al. |
| 5,084,586 A | 1/1992 | Farooq |
| 5,089,374 A | 2/1992 | Saeva |
| 5,105,006 A | 4/1992 | Parker |
| 5,124,417 A | 6/1992 | Farooq |
| 5,130,347 A | 7/1992 | Mitra |
| 5,154,762 A | 10/1992 | Mitra et al. |
| 5,256,447 A | 10/1993 | Oxman et al. |
| 5,304,585 A | 4/1994 | Bunker |
| 5,486,544 A | 1/1996 | Kawashima |
| 5,501,727 A | 3/1996 | Wang et al. |
| 5,530,038 A | 6/1996 | Yamamoto et al. |
| 5,545,676 A | 8/1996 | Palazzotto et al. |
| 5,607,663 A | 3/1997 | Rozzi et al. |
| 5,662,887 A | 9/1997 | Rozzi et al. |
| 5,866,630 A | 2/1999 | Mitra et al. |
| 5,876,208 A | 3/1999 | Mitra et al. |
| 5,888,491 A | 3/1999 | Mitra et al. |

(Continued)

FOREIGN PATENT DOCUMENTS

DE    1138226    10/1962

(Continued)

OTHER PUBLICATIONS

Crivello et al., "Dye-Sensitized Photoinitiated Cationic Polymerization. The System: Perylene-Triarylsulfonium Salts", *General Electric Corporate Research and Development*, Schenectady, NY, pp. 1059-1065, (2003).

"Pigments-Inorganic" and "Pigments-Organic", *Kirk-Othmer Encyclopedia of Chemical Technology*, Third ed., vol. 17, pp. 788-871, John Wiley & Sons, NY, 1982.

Pearson, "Photoconductive Polymers", *Pure and Appl. Chem.*, 49, pp. 463-477, 1977.

Beringer et al., "Diaryliodonium Salts. IX. The Synthesis of Substituted Diphenyliodonium Salts", *Am. Chem. Soc.*, 81, 342-351 (1959).

(Continued)

*Primary Examiner*—Tae H Yoon
(74) *Attorney, Agent, or Firm*—Sean J. Edman

(57) ABSTRACT

Polymerizable compositions and methods are provided that include an ethylenically unsaturated compound and an arylsulfinate salt. The polymerizable compositions are useful as hardenable dental compositions.

21 Claims, No Drawings

U.S. PATENT DOCUMENTS

| | | | |
|---|---|---|---|
| 5,998,495 | A | 12/1999 | Oxman et al. |
| 6,017,660 | A | 1/2000 | Palazzotto et al. |
| 6,030,606 | A | 2/2000 | Holmes |
| 6,187,833 | B1 | 2/2001 | Oxman et al. |
| 6,204,302 | B1 | 3/2001 | Rawls et al. |
| 6,312,668 | B2 | 11/2001 | Mitra et al. |
| 6,331,080 | B1 | 12/2001 | Cole et al. |
| 6,387,981 | B1 | 5/2002 | Zhang et al. |
| 6,444,725 | B1 | 9/2002 | Trom et al. |
| 6,458,868 | B1 | 10/2002 | Okada et al. |
| 6,528,555 | B1 | 3/2003 | Nikutowski et al. |
| 6,572,693 | B1 | 6/2003 | Wu et al. |
| 6,759,177 | B2 | 7/2004 | Shimada et al. |
| 7,030,169 | B2* | 4/2006 | Kalgutkar et al. ............ 522/31 |
| 7,064,152 | B2* | 6/2006 | Kalgutkar et al. ............ 522/15 |
| 2003/0054288 | A1 | 3/2003 | Shimada et al. |
| 2005/0070624 | A1* | 3/2005 | Kalgutkar et al. ............ 522/7 |
| 2006/0111462 | A1* | 5/2006 | Kalgutkar et al. ............ 522/31 |

FOREIGN PATENT DOCUMENTS

| | | |
|---|---|---|
| EP | 0 201 031 | 11/1986 |
| EP | 0 201 778 | 11/1986 |
| EP | 0 237 233 | 9/1987 |
| EP | 0 373 384 | 6/1990 |
| EP | 0375160 | 6/1990 |
| EP | 0 712 622 | 5/1996 |
| EP | 1 051 961 | 11/2000 |
| EP | 1269967 | 1/2003 |
| GB | 1205709 | 9/1970 |
| JP | 61101513 | 5/1986 |
| JP | 9034110 A | 2/1997 |
| JP | 2002341519 A | 11/2002 |
| WO | WO 00/38619 | 7/2000 |
| WO | WO 00/42092 | 7/2000 |
| WO | WO 01/07444 | 2/2001 |
| WO | WO 01/30306 | 5/2001 |
| WO | WO 01/30307 | 5/2001 |
| WO | WO 01/92271 | 12/2001 |
| WO | WO 02/092021 | 11/2002 |

OTHER PUBLICATIONS

Dorman et al., "Carbon-13 Nuclear Magnetic Resonance Spectroscopy. Quantitative Correlations of the Carbon Chemical Shifts of Acyclic Alkenes", *J. Org. Chem.*, 36, 2757-2766 (1971).

Sims et al., "Studies on the Mechanism by Which Cyanine Dyes Measure Membrane Potential in Red Blood Cells and Phosphatidylcholine Vesicles", *Biochemistry*, vol. 13, No. 16, 3315-3330 (1974).

Paushkin et al., *Organic Polymeric Semiconductors*, Table of Contents, John Wiley & Sons, New York, (1974).

Overbeek et al., "Microemulsions", *Surfactants*, Table of Contents, Academic Press (1984).

F.J. Green, *The Sigma-Aldrich Handbook of Stains, Dyes, and Indicators*, Table of Contents, Aldrich Chemical Company, Inc., (1990).

Safran et al., "Phase Diagrams for Microemulsions", *Phys.Rev.Lett.*, vol. 50, No. 24, pp. 1930-1933, (1983).

Buonocore et al., "A Report on A Resin Composition Capable Of Bonding To Human Dentin Surfaces", *J.Dent.Res.*, vol. 35, No. 6, pp. 846-851, (1956).

Leung et al., "Microemulsions: Formation, Structure, Properties, and Novel Applications", *Microemulsions*, Chapter 9, pp. 315-366., (1988).

Ostrovsky et al., "Mechanism of Microemulsion Formation In Systems With Low Interfacial Tension: Occurrence, Properties, and Behavior of Microemulsions", *J.Colloid.Interface.Sci.*, vol. 102, No. 1, pp. 206-226 (1984).

Palazzotto et al., U.S. Appl. No. 10/328,520, "*Curing Agents for Cationically Curable Compositions*", filed Dec. 23, 2002.

Connors, K. A.., "Chemical Kinetics, The Study of Reaction Rates in Solution", *VCH*, 1990, Chapter 2.

Rodrigues et al., "Cationic Photopolymerization Of Tetrahydrofuran: A Mechanistic Study On The Use Of A Sulfonium Salt-Phenothiazine Initiation System", *Journal of Polymer Science: Part A: Polymer Chemistry*, vol. 39, pp. 46-55, 2001.

Gomurashvili et al., "Phenothiazine Photosensitizers For Onium Salt Photoinitiated Cationic Polymerization", *Journal of Polymer Science: Part A: Polymer Chemistry*, vol. 39, pp. 1187-1197, 2001.

* cited by examiner

DENTAL COMPOSITIONS AND METHODS WITH ARYLSULFINATE SALTS

BACKGROUND

Polymerizable compositions are used for a wide variety of dental and orthodontic applications, including, for example, primers, dental adhesives, orthodontic adhesives, coatings, sealants, cements, compomers, restoratives, and combinations thereof. For example, polymerizable dental adhesives are typically used to bond dental materials (e.g., restorative materials such as cured or uncured composites such as glass ionomer cements, modified glass ionomer cements, etc.; fillings; sealants; inlays; onlays; crowns; bridges; etc.) to the relevant dental structures. Similarly, orthodontic adhesives are used in the bonding of orthodontic appliances (e.g., brackets, buccal tubes, bands, cleats, buttons, lingual retainers, and bite blockers) to a dental structure.

Polymerizable compositions useful in dental and orthodontic applications typically include a polymerizable component and an initiator system. Commonly, the initiator system induces the free radical polymerization of an ethylenically unsaturated polymerizable component, resulting in hardening of the composition. In some polymerizable compositions, polymerization may be induced by irradiating the composition. In other polymerizable compositions, polymerization may be induced by combining separate components of the initiator system.

It is desirable for polymerizable compositions useful in dental and orthodontic applications to have sufficient stability (e.g., physical or chemical stability) before polymerization, but to harden readily upon inducement of polymerization. Although the nature of the initiator system generally influences the desired balance of properties, it is also desirable that the initiator system be useful in a variety of dental compositions (e.g., one-part compositions, two-part compositions, acidic compositions, etc.). In addition, it is desirable that the initiator system does not produce an undesirable color change during or after polymerization. Preferred embodiments of the present invention meet some of these needs.

SUMMARY OF THE INVENTION

The present invention provides polymerizable compositions that can be useful as dental materials suitable for use in the oral environment, and methods of using such compositions. The polymerizable compositions include an ethylenically unsaturated compound and an initiator system. In some embodiments, the polymerizable composition includes a dental additive (e.g., a photobleachable dye). The polymerizable composition can be in the form of a dispersion, a suspension, an emulsion, a solution, or a combination thereof. Preferably, the polymerizable composition is chemically stable. The polymerizable composition may be, for example, a primer, a dental adhesive, an orthodontic adhesive, a coating, a sealant, a cement, a restorative, or a combination thereof.

The initiator system includes an arylsulfinate salt having an anion of Formula I

$$Ar^1\text{—}SO_2^-  \quad\quad\quad I$$

and a cation having a positively charged nitrogen atom or a positively charged phosphorus atom, wherein the arylsulfinate salt has an oxidation potential in N,N-dimethylformamide of 0.0 to +0.4 volts versus a silver/silver nitrate reference electrode, and wherein $Ar^1$ is a $C_{6-30}$ aryl or a $C_{3-30}$ heteroaryl that is unsubstituted or substituted with an electron withdrawing group or an electron withdrawing group in combination with an electron donating group. Preferably, the arylsulfinate salt is miscible with the ethylenically unsaturated compound in the polymerizable composition.

In some embodiments, the initiator system further includes a sensitizer, an electron acceptor, and/or a reducing agent different from the arylsulfinate salt. Preferably, the sensitizer is capable of absorbing a wavelength of actinic radiation in the range of 250 to 1000 nanometers. Preferably, the electron acceptor has a reduction potential in N,N-dimethylformamide of +0.4 to −1.0 volts versus a silver/silver nitrate reference electrode.

The present invention further provides methods of hardening polymerizable compositions as disclosed herein. The methods disclosed herein can be useful for treating a dental structure surface by applying a hardenable dental composition to the dental structure surface, and hardening the composition.

In one embodiment, the present invention provides a method of hardening a polymerizable composition in which the initiator system, as described herein above, further includes a sensitizer capable of absorbing a wavelength of actinic radiation in the range of 250 to 1000 nanometers. The method includes irradiating a polymerizable composition. Optionally, the initiator system further includes an electron acceptor having a reduction potential in N,N-dimethylformamide of +0.4 to −1.0 volts versus a silver/silver nitrate reference electrode.

In another embodiment, the present invention provides a method of hardening a polymerizable composition in which the initiator system, as described herein above, further includes an electron acceptor having a reduction potential in N,N-dimethylformamide of +0.4 to −1.0 volts versus a silver/silver nitrate reference electrode. The method includes: combining components of the polymerizable composition to form a hardenable dental composition, and allowing the dental composition to harden. Optionally, the initiator system further includes a sensitizer capable of absorbing a wavelength of actinic radiation in the range of 250 to 1000 nanometers. Optionally, the method further includes irradiating the hardenable dental composition.

In another aspect, the present invention provides self-etching, polymerizable dental compositions and/or self-adhesive, polymerizable dental compositions. Optionally, the compositions are non-aqueous. Optionally, the compositions can include a filler, which can be a nanofiller. In some embodiments the compositions can include water and a surfactant (e.g., a non-ionic surfactant and/or a polymerizable surfactant), and the compositions can be emulsions (e.g., water-in-oil emulsions and/or microemulsions). In some embodiments, the emulsions include less than 30% by weight water. Preferably, the compositions are physically and/or chemically stable. Optionally, the compositions include a dental additive (e.g., a photobleachable dye).

In one embodiment, the present invention provides a self-etching, polymerizable dental composition that includes: an ethylenically unsaturated compound with acid functionality; an ethylenically unsaturated compound without acid functionality; and an initiator system, as described herein above. The acid functionality can include carboxylic acid functionality, phosphoric acid functionality, sulfonic acid functionality, or combinations thereof.

In another embodiment, the present invention provides a self-adhesive, polymerizable dental composition that includes: an ethylenically unsaturated compound with acid functionality; an ethylenically unsaturated compound without acid functionality; an initiator system as described herein above, and at least 40% by weight filler. Optionally, the composition is self-etching.

Definitions

As used herein, the term "actinic radiation" refers to electromagnetic radiation capable of producing photochemical activity.

As used herein, the term "acyl" refers to a monovalent group of formula —(CO)$R^a$ where $R^a$ is an alkyl or aryl group.

As used herein, the term "alkenyl" refers to a monovalent radical of an alkene (i.e., an alkene is an aliphatic compound having at least one carbon-carbon double bond).

As used herein, the term "alkoxy" refers to a group of formula —OR where R is an alkyl group. Examples include methoxy, ethoxy, propoxy, butoxy, and the like.

As used herein, the term "alkoxycarbonyl" refers to a monovalent group of formula —(CO)OR where R is an alkyl group. An example is ethoxycarbonyl.

As used herein, the term "alkoxysulfonyl" refers to a monovalent group having the formula —$SO_3R$ where R is an alkyl group.

As used herein, the term "alkynyl" refers to a monovalent radical of an alkyne (i.e., an alkyne is an aliphatic compound having at least one carbon-carbon triple bond).

As used herein, the term "alkyl" refers to a monovalent radical of an alkane. The alkyl can be linear, branched, cyclic, or combinations thereof and typically contains 1 to 30 carbon atoms. In some embodiments, the alkyl group contains 1 to 20, 1 to 14, 1 to 10, 4 to 10, 4 to 8, 1 to 6, or 1 to 4 carbon atoms. Examples of alkyl groups include, but are not limited to methyl, ethyl, n-propyl, isopropyl, n-butyl, tert-butyl, isobutyl, n-pentyl, n-hexyl, cyclohexyl, n-octyl, n-heptyl, and ethylhexyl.

As used herein, the term "alkylsulfonyl" refers to a monovalent group of formula —$SO_2R$ where R is an alkyl group.

As used herein, the term "amino" refers to a monovalent group of formula —$NR^b{}_2$ where each $R^b$ is independently a hydrogen, alkyl, or aryl group. In a primary amino group, each $R^b$ group is hydrogen. In a secondary amino group, one of the $R^b$ groups is hydrogen and the other $R^b$ group is either an alkyl or aryl. In a tertiary amino group, both of the $R^b$ groups are an alkyl or aryl.

As used herein, the term "aminocarbonyl" refers to a monovalent group of formula —(CO)$NR^b{}_2$ where each $R^b$ is independently a hydrogen, alkyl, or aryl.

As used herein, the term "aromatic" refers to both carbocyclic aromatic compounds or groups and heteroaromatic compounds or groups. A carbocyclic aromatic compound is a compound that contains only carbon atoms in an aromatic ring structure. A heteroaromatic compound is a compound that contains at least one heteroatom selected from S, O, N, or combinations thereof in an aromatic ring structure.

As used herein, the term "aryl" refers to a monovalent aromatic carbocyclic radical. The aryl can have one aromatic ring or can include up to 5 carbocyclic ring structures that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

As used herein, the term "aryloxy" refers to a monovalent group of formula —OAr where Ar is an aryl group.

As used herein, the term "aryloxycarbonyl" refers to a monovalent group of formula —(CO)OAr where Ar is an aryl group.

As used herein, the term "aryloxysulfonyl" refers to a monovalent group having the formula —$SO_3Ar$ where Ar is an aryl group.

As used herein, the term "azo" refers to a divalent group of formula —N=N—.

As used herein, the term "carbonyl" refers to a divalent group of formula —(CO)— where the carbon atom is connected to the oxygen atom by a double bond.

As used herein, the term "carboxy" refers to a monovalent group of formula —(CO)OH.

As used herein, the term "conjugated" refers to unsaturated compounds having at least two carbon-carbon double or triple bonds with alternating carbon-carbon single bonds and carbon-carbon double or triple bonds.

As used herein, the term "cyano" refers to a group of formula —CN.

As used herein, the term "dialkylphosphonato" refers to a group of formula —(PO)(OR)$_2$ where R is an alkyl. As used herein the formula "(PO)" indicates that the phosphorus atom is attached to an oxygen atom with a double bond.

As used herein, the term "diarylphosphonato" refers to a group of formula —(PO)(O$Ar^b$)$_2$ where $Ar^b$ is a heteroaryl.

As used herein, the term "electron donating" refers to a substituent that can donate electrons. Suitable examples include, but are not limited to, a primary amino, secondary amino, tertiary amino, hydroxy, alkoxy, aryloxy, alkyl, or combinations thereof.

As used herein, the term "electron withdrawing" refers to a substituent that can withdraw electrons. Suitable examples include, but are not limited to, a halo, cyano, fluoroalkyl, perfluoroalkyl, carboxy, aminocarbonyl, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, or combinations thereof.

As used herein, the term "fluoroalkyl" refers to an alkyl group that has at least one hydrogen atom replaced with a fluorine atom.

As used herein, the term "formyl" refers to a monovalent group of formula —(CO)H where the carbon is attached to the oxygen atom with a double bond.

As used herein, the term "halo" refers to a halogen group (i.e., F, Cl, Br, or I). In some embodiments, the halo group is F or Cl.

As used herein, the term "halocarbonyl" refers to a monovalent group of formula —(CO)X where X is a halogen group (i.e., F, Cl, Br, or I).

As used herein, the term "heteroaryl" refers to a monovalent radical having a five to seven member aromatic ring that includes one or more heteroatoms independently selected from S, O, N, or combinations thereof in the ring. Such a heteroaryl ring can be connected to or fused to up to five ring structures that are aromatic, aliphatic, or combinations thereof. Examples of heteroaryl groups include, but are not limited to, quinolinyl, isoquinolinyl, quinazolinyl, quinoxalinyl, cinnolinyl, benzofuranyl, benzomercaptophenyl, benzoxazolyl, benzothiazolyl, benzimidazolyl, indolyl, phthalazinyl, benzothiadiazolyl, benzotriazinyl, phenazinyl, phenanthridinyl, acridinyl, and indazolyl, and the like. A heteroaryl is a subset of a heterocyclic group.

As used herein, the term "heterocyclic" refers to a monovalent radical having a ring structure that is saturated or unsaturated and that includes one or more heteroatoms independently selected from S, O, N, or combinations thereof in the ring. The heterocyclic group can be a single ring, bicyclic, or can be fused to another cyclic or bicyclic group. The fused cyclic or bicyclic group can be saturated or unsaturated and can be carbocyclic or contain heteroatoms.

As used herein, the term "hydroxy" refers to a group of formula —OH.

As used herein, the term "mercapto" refers to a group of formula —SH.

As used herein, the term "perfluoroalkyl" refers to an alkyl group that has all the hydrogen atoms replaced with fluorine atoms. A perfluoroalkyl is a subset of a fluoroalkyl.

As used herein, the term "perfluoroalkylsulfonyl" refers to a monovalent group of formula —$SO_2R_f$ where $R_f$ is a perfluoroalkyl.

As used herein, the term "sulfo" refers to a group having the formula —$SO_3H$.

As used herein, "adhesive" or "dental adhesive" refers to a composition used as a pre-treatment on a dental structure (e.g., a tooth) to adhere a "dental material" (e.g., "restorative," an orthodontic appliance (e.g., bracket), or an "orthodontic adhesive") to the dental structure. An "orthodontic adhesive" refers to a highly (generally greater than 40% by weight) filled composition (more analogous to a "restorative material" than to a "dental adhesive") used to adhere an orthodontic appliance to a dental structure (e.g., tooth) surface. Generally, the dental structure surface is pre-treated, e.g., by etching, priming, and/or applying an adhesive to enhance the adhesion of the "orthodontic adhesive" to the dental structure surface.

As used herein, a "non-aqueous" composition (e.g., an adhesive) refers to a composition in which water has not been added as a component. However, there may be adventitious water in other components of the composition, but the total amount of water does not adversely affect stability (e.g., the shelf-life) of the non-aqueous composition. Non-aqueous compositions preferably include less than 1% by weight, more preferably less than 0.5% by weight, and most preferably less than 0.1% by weight water, based on the total weight of the non-aqueous composition.

As used herein, a "self-etching" composition (or self-etching adhesive composition) refers to a composition that bonds to a dental structure surface without pretreating the dental structure surface with an etchant. Preferably, a self-etching composition can also function as a self-primer wherein no separate etchant or primer are used.

As used herein, a "self-adhesive" composition (or self-adhesive composite) refers to a composition that is capable of bonding to a dental structure surface without pretreating the dental structure surface with a primer or bonding agent. Preferably, a self-adhesive composition is also a self-etching composition wherein no separate etchant is used.

As used herein, "hardening" or "curing" a composition are used interchangeably and refer to polymerization and/or crosslinking reactions including, for example, photopolymerization reactions and chemical polymerization techniques (e.g., ionic reactions) involving one or more materials included in the composition.

As used herein, a "dental structure surface" refers to tooth structures (e.g., enamel and dentin) and bone.

As used herein, "miscible" means at least partially soluble.

As used herein, an "oil-in-water" emulsion refers to an oil-in-water mixture in which the water forms a continuous phase and the oil is in discontinuous droplets.

As used herein, a "water-in-oil" emulsion refers to a water-in-oil mixture in which the oil forms a continuous phase and the water is in discontinuous droplets. A water-in-oil emulsion can be distinguished from an oil-in-water emulsion by using an electrical emulsion tester according to the method described in U.S. Provisional Application Ser. No. 60/494,603, filed Aug. 12, 2003. An oil-in-water emulsion will conduct electricity with relatively low resistance since water forms its external or continuous phase, whereas a water-in-oil emulsion will not conduct, or very poorly conduct, electricity.

As used herein, "oil phase" in a water-in-oil emulsion refers to all components in the formulation that individually exceed their solubility limit in the water phase; these are materials that generally have solubilities of less than 1% in distilled water, however, water phase components such as salts may decrease the solubility of certain oils resulting in their partitioning into the oil phase.

As used herein, "water phase" in a water-in-oil emulsion refers to the water present and any components that are water soluble, i.e., have not exceeded their solubility limit in water.

As used herein, a "physically stable" emulsion refers to an emulsion that has no visible water separation following one (preferably, two, and more preferably, three) freeze/thaw/centrifuging cycles according to the Emulsion Stability Test Protocol as described in U.S. Provisional Application Ser. No. 60/494,603, filed Aug. 12, 2003.

As used herein, a "chemically stable" or "shelf-stable" compound or composition refers to a compound or composition that has a shelf-life of at least one year, and preferably at least 2 years, at room temperature. Shelf-life of a self-adhesive composition is typically measured by determining if the aged composition provides acceptable bond strengths when the aged composition is bonded to a dental structure surface.

As used herein, a "surfactant" refers to a surface-active agent that modifies the nature of a surface (e.g., reduces the surface tension) and encompasses surface-active agents typically referred to as "wetting agents."

As used herein, "a" or "an" means "at least one" or "one or more" unless otherwise indicated.

DETAILED DESCRIPTION OF PREFERRED EMBODIMENTS

Dental compositions of the present invention include an ethylenically unsaturated compound and an arylsulfinate salt. Preferably, the arylsulfinate salt is miscible, and more preferably soluble at the level used, in the ethylenically unsaturated compound. In some embodiments, it is preferable that the arylsulfinate salt is at least 1 wt-%, more preferably at least 5 wt-%, and most preferably at least 10 wt-% soluble in the ethylenically unsaturated compound. In contrast, metal salts of arylsulfinates are generally insoluble in ethylenically unsaturated compounds useful for dental compositions.

Generally, the arylsulfinate salt is part of an initiator system that may or may not include components in addition to the arylsulfinate salt. Such components include, for example, a sensitizer, an electron acceptor, a reducing agent different from the arylsulfinate salt (e.g., a secondary reducing agent), and combinations therof. Initiator systems can be thermal initiator systems, photoinitiator systems, or combinations thereof.

In some embodiments of the present invention, the dental composition further includes a dental additive. Some embodiments of the present invention include dental additives such as fillers, surfactants, emulsifiers, and photobleachable dyes.

Dental compositions of the present invention may be in the form of a dispersion, a suspension, an emulsion, a solution, and combinations thereof. In some embodiments of the present invention, the dental composition can be a water-in-oil emulsion. Dental compositions can be, for example, resin-modified glass ionomer cements, conventional methacrylate composites, compomers, and combinations thereof.

The dental compositions of the present invention can be useful as primers (including self-etching primers), adhesives (including self-etching adhesives), orthodontic adhesives, coatings, sealants, cements, and restoratives (including fillings, composites, flowables, and prostheses such as crowns, bridges, veneers, inlays, onlays, and the like). Dental prostheses typically are filled composites that are shaped and polymerized for final use before being disposed adjacent to a tooth. Such preformed articles can be ground or otherwise formed into a custom-fitted shape by the dentist or other user. When used as primers, adhesives, or cements, the dental compositions can be utilized for adhering a restorative (cured or uncured) to a dental structure surface. When used as an orthodontic adhesive, the dental composition can be utilized for adhering an orthodontic appliance (e.g., a bracket, a buccal tube, a band, a cleat, a button, a lingual retainer, or a bite blocker) to a dental structure surface.

Initiator Systems

Aryl Sulfinate Salts

A variety of materials are known for use as an electron donor in initiator systems for polymerization reactions. However, some of these materials are not stable enough to be used in a photoinitiator system. That is, some of these materials cannot be mixed with an electron acceptor and/or a sensitizing compound for an extended period (e.g., more than a day) prior to activation of the initiator system. Further, some of these materials that would be suitable as electron donors in photoinitiator systems based on their oxidation potential and stability have limited solubility in ethylenically unsaturated compounds.

One aspect of the invention provides a composition that includes an electron donor, an electron acceptor, and optionally a sensitizer. Another aspect of the invention provides a composition that includes an electron donor and a sensitizer. More specifically, the electron donor includes an arylsulfinate salt. The compositions can be used as initiator systems for free radical polymerization reactions. The initiator systems can be used in photopolymerization methods, thermal polymerization methods, or combinations thereof. Thermal polymerization methods include typical redox methods, i.e., methods that utilize an electron donor (typically a reducing agent) and an electron acceptor (typically an oxidizing agent); and typically can be polymerized at room temperature after the reducing agent and oxidizing agent are brought into contact with each other.

The electron donor has an oxidation potential in N,N-dimethylformamide of 0.0 to +0.4 volts versus a silver/silver nitrate reference electrode and is an arylsulfinate salt having an anion of Formula I $$Ar^1-SO_2^-$$  I and a cation that includes a positively charged nitrogen atom or a positively charged phosphorus atom. Preferably the cation has at least one carbon atom. The $Ar^1$ group in Formula I is a $C_{6-30}$ aryl or a $C_{3-30}$ heteroaryl that is unsubstituted or substituted with an electron withdrawing group or an electron withdrawing group in combination with an electron donating group. The electron acceptor has a reduction potential in N,N-dimethylformamide of +0.4 to −1.0 volts versus a silver/silver nitrate reference electrode.

The electron donor is selected to have an oxidation potential and the electron acceptor is selected to have a reduction potential in a stated range. The oxidation and reduction potentials can be determined using cyclic voltammetry. As described in U.S. patent application Ser. No. 10/672,762, filed Sep. 26, 2003 (now U.S. Pat. No. 7,030,169 (Kalgutkar et al.)), the oxidation and reduction potentials are measured by dissolving the compound of interest in a non-aqueous solvent (i.e., N,N-dimethylformamide) containing a supporting electrolyte (i.e., 0.1 moles/liter tetrabutylammonium hexafluorophosphate). The resulting solution is purged with an inert gas such as argon. A three-electrode configuration is used that includes a working electrode (i.e., a glassy carbon electrode), a reference electrode (i.e., a silver wire in a 0.01 moles/liter solution of silver nitrate dissolved in acetonitrile), and a counter electrode (i.e., a platinum wire). The oxidation or reduction potential is the voltage corresponding to the maximum current for the oxidation or reduction reaction.

In the present invention, the electron donor is an arylsulfinate salt having an anion of Formula I:

$$Ar^1-SO_2^-$$  I and a cation that includes a positively charged nitrogen atom or a positively charged phosphorus atom. Preferably the cation has at least one carbon atom. The $Ar^1$ group in Formula I can be a $C_{6-30}$ aryl or a $C_{3-30}$ heteroaryl that is unsubstituted or substituted with an electron withdrawing group or an electron withdrawing group in combination with an electron donating group. The arylsulfinate salt is typically soluble in ethylenically unsaturated compounds capable of undergoing free radical polymerization reactions and in a variety of non-polar and polar solvents. As used herein, the term "soluble" refers to a compound that can be dissolved in an amount at least equal to 0.1 moles/liter in a given material such as a solvent or ethylenically unsaturated compound.

In some arylsulfinate salts, the $Ar^1$ group is an aryl group having a carbocyclic aromatic ring. The aryl group can have a single carbocyclic aromatic ring or can have additional carbocyclic rings that are fused or connected to the carbocyclic aromatic ring. Any fused or connected rings can be saturated or unsaturated. The aryl often contains up to 5 rings, up to 4 rings, up to 3 rings, up to 2 rings, or one ring. The aryl group usually has up to 30 carbon atoms, up to 24 carbon atoms, up to 18 carbon atoms, up to 12 carbon atoms, or 6 carbon atoms. Examples of aryl groups having a single ring or multiple fused rings include, but are not limited to, phenyl, anthryl, naphthyl, acenaphthyl, phenanthryl, phenanthrenyl, perylenyl, and anthracenyl. A single bond, methylene group (i.e., —CH$_2$—), carbonyl group (i.e., —(CO)—), or combinations thereof can connect multiple rings. Examples of aryl groups having multiple connected rings include, but are not limited to, anthraquinonyl, anthronyl, biphenyl, terphenyl, 9,10-dihydroanthracenyl, and fluorenyl.

In other arylsulfinate salts, the $Ar^1$ group in Formula I can be a heteroaryl that has a five to seven member aromatic ring that includes one or more heteroatoms independently selected from S, O, N, or combinations thereof in the ring. The heteroaryl can have a single ring or can have multiple rings connected or fused together. Any additional connected or fused rings can be carbocyclic or contain a heteroatom and can be saturated or unsaturated. The heteroaryl group often has up to 5 rings, up to 4 rings, up to 3 rings, up to 2 rings, or one ring. The heteroaryl typically contains up to 30 carbon atoms. In some embodiments, the heteroaryl contains up to 20 carbon atoms, up to 10 carbon atoms, or up to 5 carbon atoms. Examples of heteroaryl groups include, but are not limited to, quinolinyl, isoquinolinyl, quinazolinyl, quinoxalinyl, cinnolinyl, benzofuranyl, benzomercaptophenyl, benzoxazolyl, benzothiazolyl, benzimidazolyl, indolyl, phthalazinyl, benzothiadiazolyl, benzotriazinyl, phenazinyl, phenanthridinyl, acridinyl, azaphenanthrenyl, and indazolyl.

The $Ar^1$ group in Formula I can be unsubstituted or substituted with an electron withdrawing group or an electron withdrawing group in combination with an electron donating group provided that the arylsulfinate salt has an oxidation potential in N,N-dimethylformamide of 0.0 to +0.4 volts versus a silver/silver nitrate reference electrode. Electron donating groups can be selected, for example, from a primary amino, secondary amino, tertiary amino, hydroxy, alkoxy, aryloxy, alkyl, or combinations thereof. Electron withdrawing groups can be selected, for example, from a halo, cyano, fluoroalkyl, perfluoroalkyl, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, diarylphosphonato, or combinations thereof.

In some embodiments, the $Ar^1$ group includes an electron withdrawing group that is conjugated to the sulfinate group. For example, the $Ar^1$ group can be a phenyl substituted with an electron withdrawing group selected from halo, cyano, fluoroalkyl, perfluoroalkyl, carboxy, aminocarbonyl, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, or combinations thereof.

Specific examples of the arylsulfinate anion of Formula I include, but are not limited to, 4-chlorobenzenesulfinate, 4-cyanobenzenesulfinate, 4-ethoxycarbonylbenzenesulfinate, 4-trifluoromethylbenzenesulfinate, 3-trifluoromethylbenzenesulfinate, 1-naphthalenesulfinate, 2-naphthalenesulfinate, and 1-anthraquinonesulfinate.

The arylsulfinate salts have a cation with a positively charged nitrogen atom or a positively charged phosphorus atom. Preferably the cation has at least one carbon atom. In one embodiment, the cation of the arylsulfinate is of Formula II:

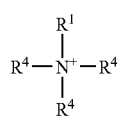

where $R^1$ is an alkyl or aryl and each $R^4$ is independently a hydrogen, alkyl, or aryl. The $R^1$ and $R^4$ groups can be unsubstituted or substituted. An alkyl group can be substituted with a hydroxy. An aryl can be substituted with an alkyl, hydroxy, or combinations thereof.

In some examples of Formula II, $R^1$ and each $R^4$ group are independently a $C_{2-30}$ alkyl that is unsubstituted or substituted with a hydroxy. For example, $R^1$ and each $R^4$ independently can be an alkyl group having up to 20, up to 10, up to 8, up to 6, or up to 4 carbon atoms. The alkyl group often has at least 2, at least 3, at least 4, at least 6, or at least 8 carbon atoms. The alkyl group can have 4 to 30, 8 to 30, 3 to 10, 4 to 10, 4 to 8, or 4 to 6 carbon atoms in some compounds. In a specific example, the cation of the arylsulfinate salt is a tetrabutylammonium ion.

In other examples of Formula II, $R^1$ and two $R^4$ groups are each independently a $C_{2-30}$ alkyl that can be unsubstituted or substituted with a hydroxy. The remaining $R^4$ group is hydrogen. In still other examples, $R^1$ and one $R^4$ group are each independently a $C_{4-30}$ alkyl that is unsubstituted or substituted with a hydroxy; and the two remaining $R^4$ groups are hydrogen. In yet other examples, $R^1$ is a $C_{8-30}$ alkyl that is unsubstituted or substituted with a hydroxy; and the $R^4$ groups are hydrogen.

The $R^1$ group and each of the $R^4$ groups in Formula II independently can be an aryl group that is unsubstituted or substituted with an alkyl, hydroxy, or combinations thereof. An exemplary cation is tetraphenylammonium ion. In another example, $R^1$ and one $R^4$ are independently an aryl group that is unsubstituted or substituted with an alkyl, hydroxy, or combinations thereof; and the two remaining $R^4$ groups are hydrogen. An exemplary cation is diphenylammonium ion.

In other embodiments, the cation of the arylsulfinate salt is a ring structure that includes a four to twelve member heterocyclic group with a positively charged nitrogen atom. The heterocyclic group can be saturated or unsaturated and can contain up to three heteroatoms selected from nitrogen, oxygen, sulfur, or combinations thereof (i.e., there is one positively charged nitrogen atom and up to two other heteroatoms selected from nitrogen, oxygen, sulfur, or combinations thereof). The ring structure can be unsubstituted or have a substituent selected from an alkyl, aryl, acyl, alkoxy, aryloxy, halo, mercapto, amino, hydroxy, azo, cyano, carboxy, alkoxycarbonyl, aryloxycarbonyl, halocarbonyl, or combinations thereof.

The heterocyclic group in the cationic ring structure can be a single ring, bicyclic, or can be fused to another cyclic or bicyclic group. The fused cyclic or bicyclic group can be saturated or unsaturated and can have 0 to 3 heteroatoms. The ring structure can include up to 30 carbon atoms, up to 24 carbon atoms, up to 18 carbon atoms, up to 12 carbon atoms, up to 6 carbon atoms, or up to 4 carbon atoms and up to 6 heteroatoms, up to 4 heteroatoms, up to 2 heteroatoms, or 1 heteroatom. In some embodiments, the ring structure is a 4 to 12 member heterocyclic group that is a fused to an aromatic ring having 0 to 3 heteroatoms.

Suitable examples of five member heterocyclic groups that contain a positively charged nitrogen atom include, but are not limited to, a pyrrolium ion, pyrazolium ion, pyrrolidinium ion, imidazolium ion, triazolium ion, isoxazolium ion, oxazolium ion, thiazolium ion, isothiazolium ion, oxadiazolium ion, oxatriazolium ion, dioxazolium ion, and oxathiazolium ion. These ions can be unsubstituted or substituted with an alkyl, aryl, acyl, alkoxy, aryloxy, halo, mercapto, amino, hydroxy, azo, cyano, carboxy, alkoxycarbonyl, aryloxycarbonyl, halocarbonyl group, or combinations thereof. In some applications, the cation is an imidazolium ion or oxazolium ion that is unsubstituted or substituted.

The five member heterocyclic groups can be fused to another cyclic group. In some exemplary ring structures, a five membered heterocyclic group is fused to an aromatic group. Exemplary ring structures include, but are not limited to, an indole ion, indazolium ion, benzopyrrolidinium ion, benzimidazolium ion, benzotriazolium ion, benzisoxazolium ion, benzoxazolium ion, benzothiazolium ion, benzisothiazolium ion, benzoxadiazolium ion, benzoxatriazolium ion, benzodioxazolium ion, benzoxathiazolium ion, carbozolium ion, and purinium ion. These ions can be unsubstituted or substituted with an alkyl, aryl, acyl, alkoxy, aryloxy, halo, mercapto, amino, hydroxy, azo, cyano, carboxy, alkoxycarbonyl, aryloxycarbonyl, halocarbonyl group, or combinations thereof. In some applications, the cation is a benzoxazolium ion or a benzothiazolium ion that is unsubstituted or substituted.

Suitable examples of six member heterocyclic groups that contain a positively charged nitrogen atom include, but are not limited to, a pyridinium ion, pyridazinium ion, pyrimidinium ion, pyrazinium ion, piperazinium ion, triazinium ion, oxazinium ion, piperidinium ion, oxathiazinium ion, oxadiazinium ion, and morpholinium ion. These ions can be unsubstituted or substituted with an alkyl, aryl, acyl, alkoxy, aryloxy, halo, mercapto, amino, hydroxy, azo, cyano, or carboxy, alkoxycarbonyl, aryloxycarbonyl, halocarbonyl group, or combinations thereof. In some applications, the cation is a pyridinium ion or a morpholinium ion that is unsubstituted or substituted.

The six member heterocyclic groups can be fused to another cyclic group. In some exemplary ring structures, a six membered heterocyclic group is fused to an aromatic group. Exemplary ring structures include, but are not limited to, isoquinolinium ion, quinolinium ion, cinnolinium ion, quinazolinium ion, benzopyrazinium ion, benzopiperazinium ion, benzotriazinium ion, benzoxazinium ion, benzopiperidinium ion, benzoxathiazinium ion, benzoxadizinium ion, benzomorpholinium ion, naphtyridinium ion, and acridinium ion. These ions can be unsubstituted or substituted with an alkyl, aryl, acyl, alkoxy, aryloxy, halo, mercapto, amino, hydroxy, azo, cyano, or carboxy, alkoxycarbonyl, aryloxycarbonyl, halocarbonyl group, or combinations thereof.

Suitable examples of seven member heterocyclic groups that contain a positively charged nitrogen atom include, for example, an azepinium ion and diazepinium ion. These ions can be unsubstituted or substituted with an alkyl, aryl, acyl, alkoxy, aryloxy, halo, mercapto, amino, hydroxy, azo, cyano, carboxy, alkoxycarbonyl, aryloxycarbonyl, halocarbonyl group, or combinations thereof.

Examples of heterocyclic groups that are bicyclic include, but are not limited to, N-alkylated or N-protonated 1,4-diazabicyclo[2.2.2]octane and N-alkylated or N-protonated 1-azabicyclic[2.2.2]octane that is unsubstituted or substituted with an alkyl, aryl, acyl, alkoxy, aryloxy, halo, mercapto, amino, hydroxy, azo, cyano, carboxy, alkoxycarbonyl, aryloxycarbonyl, halocarbonyl group, or combinations thereof.

In other embodiments, the cation of the arylsulfinate salt contains a positively charged phosphorus atom of Formula III:

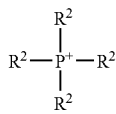

where each $R^2$ is independently an alkyl or aryl that is unsubstituted or substituted. An alkyl group can be substituted with a hydroxy. An aryl can be substituted with an alkyl, hydroxy, or combinations thereof.

In some examples of Formula III, all of the $R^2$ groups are an aryl group. For example, the cation can be a tetraphenylphosphonium ion. In other examples, one, two, or three of the $R^2$ groups are an aryl with the remaining $R^2$ group or groups being a $C_{2-30}$ alkyl.

Some of the arylsulfinate salts can have an anion of Formula IV

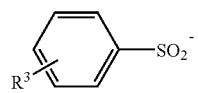

and a cation that includes a positively charged nitrogen atom. Preferably the cation has at least one carbon atom. In Formula IV, $R^3$ can be in an ortho, para, or meta position of the benzene ring and is an electron withdrawing group selected from halo, cyano, fluoroalkyl, perfluoroalkyl, carboxy, alkoxycarbonyl, aryloxycarbonyl, halocarbonyl, formyl, carbonyl, sulfo, alkoxysulfonyl, aryloxysulfonyl, perfluoroalkylsulfonyl, alkylsulfonyl, azo, alkenyl, alkynyl, dialkylphosphonato, or diarylphosphonato. In some compounds, $R^3$ is selected from cyano, carboxy, alkoxycarbonyl, aryloxycarbonyl, halocarbonyl, formyl, carbonyl, sulfo, alkoxysulfonyl, aryloxysulfonyl, perfluoroalkylsulfonyl, or alkylsulfonyl. In other compounds, $R^3$ is a halo, cyano, or alkoxycarbonyl group.

Specific examples Formula IV where $R^3$ is located in the para position of the phenyl ring include 4-cyanobenzenesulfinate, 4-chlorobenzenesulfinate, 4-ethoxycarbonylbenzenesulfinate, and 4-trifluoromethylbenzenesulfinate. A specific example of $R^3$ located in the meta position of the phenyl ring includes 3-trifluoromethylbenzenesulfinate.

For some applications, the arylsulfinate salt includes an anion of Formula IV and a cation that is a tetraalkyammonium ion. The alkyl groups of the tetraalkylammonium ion can be the same or different and typically contain 2 to 30 carbon atoms. For example, the alkyl groups can contain 4 to 30 carbon atoms, 8 to 30 carbon atoms, 3 to 10 carbon atoms, 4 to 10 carbon atoms, or 4 to 8 carbon atoms. Specific arylsulfinate salts include, but are not limited to, tetrabutylammonium 4-chlorobenzenesulfinate, tetrabutylammonium 4-cyanobenzenesulfinate, tetrabutylammonium 4-ethoxycarbonylbenzenesulfinate, tetrabutylammonium 4-trifluoromethylbenzenesulfinate, and tetrabutylammonium 3-trifluoromethylbenzenesulfinate.

Other specific examples of electron donors include, but are not limited to, tetrabutylammonium 1-naphthalenesulfinate, tetrabutylammonium 2-naphthalenesulfinate, and tetrabutylammonium 1-anthraquinonesulfinate, 1-ethyl-3-methylimidazolium 4-methylbenzenesulfinate, N,N-morpholinium 4-cyanobenzenesulfinate, 3-ethyl-2-methylbenxoxazolium 4-cyanobenzenesulfinate, 1-methyl-4-aza-1-azoniabicyclo[2.2.2]octane 4-cyanobenzenesulfinate, and N-hexadecylpyridinium 4-cyanobenzenesulfinate.

Arylsulfinate salts can be prepared by methods similar to those disclosed, for example, in Assignee's U.S. patent application Ser. No. 10/672,762, filed Sep. 26, 2003 (now U.S. Pat. No. 7,030,169 (Kalgutkar et al.)).

Preferably, the electron donor (i.e., sulfinate salt) is present in an amount of at least 0.01 wt-%, and more preferably at least 0.1 wt-%, based on the total weight (including water) of the components of the hardenable composition. Preferably, the sulfinate salt is present in an amount of no greater than 10 wt-%, and more preferably no greater than 5 wt-%, based on the total weight (including water) of the components of the hardenable composition.

Secondary Reducing Agents

In some embodiments of the present invention the electron donor (i.e arylsulfinate salt) can serve as a primary reducing agent in a redox initiator system and, optionally, there can be included a secondary reducing agent. Secondary reducing agents can be either polymerizable or nonpolymerizable. Typical secondary reducing agents include ascorbic acid, ascorbic acid derivatives, and metal complexed ascorbic acid compounds as described in U.S. Pat. No. 5,501,727 (Wang et al.); amines, especially tertiary amines, such as ethyl 4-(N,N-dimethylamino)benzoate and 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), oxalic acid, salts of a dithionite or sulfite anion, and mixtures thereof. Additional compounds that may be useful as secondary reducing agents are included among the list of electron donors described in U.S. Pat. No. 5,545,676 (Palazzotto). Preferably, the secondary reducing agent is an amine, and more preferably a tertiary amine.

Preferably, if used in the composition, the optional secondary reducing agent is present in an amount of at least 0.01 wt-%, and more preferably at least 0.05 wt-%, based on the total weight (including water) of the components of the hardenable composition. Preferably, the optional secondary reducing agent is present in an amount of no greater than 10 wt-%, and more preferably no greater than 5 wt-%, based on the total weight (including water) of the components of the hardenable composition.

Electron Acceptors

In certain embodiments of the present invention, a component of the initiator system is an electron acceptor (e.g., including oxidizing agents) having a reduction potential in N,N-dimethylformamide of at most +0.4 volts, preferably at most +0.1 volts, more preferably at most 0.0 volts, even more preferably at most −0.1 volts, and most preferably at most −0.5 volts versus a silver/silver nitrate reference electrode. In some embodiments, the electron acceptor has a reduction potential in N,N-dimethylformamide of at least −1.0 volts versus a silver/silver nitrate reference electrode.

The electron acceptor is typically selected to be soluble in the ethylenically unsaturated compounds capable of undergoing free radical polymerization reactions. Suitable electron acceptors include, for example, metal ions in an oxidized state, persulfuric acid and salts thereof, peroxides and hydroperoxides, perboric acid and salts thereof, permanganic acid and salts thereof, perphosphoric acid and salts thereof, iodonium salts, or combinations thereof.

The electron acceptor is usually not mixed with the electron donor prior to use in an initiator system if the electron acceptor is a metal ion in an oxidized state, a peroxide, a persulfate, or combinations thereof. These electron acceptors can often react with the electron donor at room temperature (i.e., 20° C. to 25° C.) or at an elevated temperature (e.g., up to 150° C.) within a relatively short period of time (e.g., less than 1 hour, less than 30 minutes, less than 10 minutes, or less than 5 minutes). Such initiator systems can be initiated without activation by light (i.e., the initiator systems are thermal (e.g., redox) systems).

Suitable electron acceptor metal ions include, for example, ions of group III metals, transition metals, and lanthanide metals. Specific metal ions include, but are not limited to, Fe(III), Co(III), Ag(I), Ag(II), Cu(II), Ce(IV), Al (III), Mo(VI), and Zn(II). Examples of suitable electron acceptor salts having such metal ions include copper (II) acetate, cobalt (III) chloride, ferric (III) chloride, and cerium (IV) sulfate.

Suitable electron acceptor peroxides include benzoyl peroxide, lauryl peroxide, and the like. Suitable hydroperoxides include cumyl hydroperoxide, t-butyl hydroperoxide, sodium peroxide, hydrogen peroxide, and amyl hydroperoxide, and the like. Suitable electron acceptor persulfate salts include, for example, sodium, potassium, cesium, ammonium, and alkyl ammonium salts.

It may be desirable to use more than one oxidizing agent or more than one aryl sulfinate salt. Small quantities of transition metal compounds may also be added to accelerate the rate of polymerization (e.g., redox cure).

The arylsulfinate salt and electron acceptor (e.g. oxidizing agent) are present in amounts sufficient to permit an adequate free-radical reaction rate. This can be evaluated by combining all of the ingredients of the hardenable composition except for the optional filler, and observing whether or not a hardened mass is obtained.

If the initiator system is used in a photopolymerization method (i.e., the initiator system is a photoinitiator system), then the optional electron acceptor, if present, is typically selected so that it does not react directly with the electron donor (i.e. arylsulfinate salt) at room temperature. In some embodiments, a composition containing an electron acceptor, an electron donor, and a sensitizer typically can be stored for at least one day prior to activation of the initiator system by light and preferably the composition is chemically stable as defined herein. Electron acceptors suitable for use in photoinitiator systems include, but are not limited to, iodonium salts, hexaarylbisimidazoles, or combinations thereof.

In some embodiments, the electron acceptor has a reduction potential in N,N-dimethylformamide of at most +0.1 volts, preferably at most 0.0 volts, more preferably at most −0.1 volts, and most preferably at most −0.5 volts versus a silver/silver nitrate reference electrode. In some embodiments, the electron acceptor has a reduction potential in N,N-dimethylformamide of at least −1.0 volts versus a silver/silver nitrate reference electrode. Electron acceptors having such reduction potentials include iodonium salts. The iodonium salts are often diaryliodonium salts. Diaryliodonium salts are usually shelf-stable. That is, the diaryliodonium salts typically do not spontaneously react or promote polymerization with an electron donor when combined with the electron donor or when combined with an electron donor and a sensitizing compound in the absence of light.

Suitable iodonium salts are described in further detail in U.S. Pat. No. 3,729,313 (Smith); U.S. Pat. No. 3,741,769 (Smith); U.S. Pat. No. 3,808,006 (Smith); U.S. Pat. No. 4,250,053 (Smith); U.S. Pat. No. 4,394,403 (Smith); U.S. Pat. No. 5,545,676 (Palazzotto et al.); and U.S. Pat. No. 5,998,495 (Oxman et al.). The iodonium salt can be a simple salt, a metal complex salt, or combinations thereof. Examples of simple salts include those having an anion such as a halide, sulfonate, carboxylate, or combinations thereof. Examples of metal complex salts include those having an anion such as hexafluorophosphate, hexafluoroarsenate, hexafluoroantimonate, pentafluorohydroxyantimonate, tetrafluoroborate, tetra(pentafluorophenyl)borate, or combinations thereof.

The iodonium metal complex salts can be prepared by metathesis of corresponding iodonium simple salts (such as, for example, diphenyliodonium chloride or diphenyliodonium bisulfite) in accordance with the teachings of Beringer et al., *J. Am. Chem. Soc.*, 81, 342 (1959). In a specific example, the metal complex salt diphenyliodonium tetrafluoroborate can be prepared by the addition of an aqueous solution containing silver fluoroborate, fluoroboric acid, and phosphorus acid to an aqueous solution of diphenyliodonium chloride. The silver halide that precipitates can be filtered off and the filtrate concentrated to yield diphenyliodonium tetrafluoroborate that may be purified by recrystallization.

The diaryliodonium simple salts can be prepared in accordance with Beringer et al., above, by various methods including coupling of two aromatic compounds with iodyl sulfate in sulfuric acid; coupling of two aromatic compounds with an iodate in acetic acid-acetic anhydride; coupling of two aromatic compounds with an iodine acrylate in the presence of an acid; or condensation of an iodoso compound (e.g., iodoso diacetate) or an iodoxy compound with another aromatic compound in the presence of an acid.

Exemplary diaryliodonium salts include diphenyliodonium chloride, diphenyliodonium tetrafluoroborate, di(4-methylphenyl)iodonium tetrafluoroborate, phenyl-4-methylphenyliodonium tetrafluoroborate, di(4-heptylphenyl)iodonium tetrafluoroborate, phenyl-4-heptylphenyliodonium tetrafluoroborate, di(3-nitrophenyl)iodonium hexafluorophosphate, di(4-chlorophenyl)iodonium hexafluorophosphate, di(naphthyl)iodonium tetrafluoroborate, di(4-trifluoromethylphenyl)iodonium tetrafluoroborate, diphenyliodonium hexafluorophosphate, di(4-methylphenyl)iodonium hexafluorophosphate, diphenyliodonium hexafluoroarsenate, di(4-phenoxyphenyl)iodonium tetrafluoroborate, phenyl-2-thienyliodonium hexafluorophosphate, 3,5-dimethylpyrazolyl-4-phenyliodonium hexafluorophosphate, diphenyliodonium hexafluoroantimonate, 2,2'-diphenyliodonium tetrafluoroborate, di(2,4-dichlorophenyl)iodonium hexafluorophosphate, di(4-bromophenyl)iodonium hexafluorophosphate, di(4-methoxyphenyl)iodonium hexafluorophosphate, di(3-carboxyphenyl)iodonium hexafluorophosphate, di(3-methodycarbonylphenyl)iodonium hexafluorophosphate, di(3-methoxysulfonylphenyl)iodonium hexafluorophosphate, di(4-acetamidophenyl)iodonium hexafluorophosphate, di(2-benzothienyl)iodonium hexafluorophosphate, diphenyliodonium hexafluoroantimonate, and diphenyliodonium tetra(pentafluorophenyl)borate.

In some applications, the electron acceptor is diphenyliodonium chloride, diphenyliodonium hexafluorophosphate, diphenyliodonium tetrafluoroborate, diphenyliodonium hexafluoroantimonate, diphenyliodonium tetra(pentafluorophenyl)borate, or combinations thereof. These diaryliodonium salts tend to promote faster reactions and to be more soluble in inert organic solvents compared to some other iodonium salts.

The initiator system can include a hexaarylbisimidazole compound as the electron acceptor. Such compounds can be synthesized as described in *J. Org. Chem.*, 36, 2762 (1971). A hexaarylbisimidazole is commercially available under the trade designation SPEEDCURE BCIM from Lambson, West Yorkshire, England.

In embodiments where the initiator system is a photoinitiator system, the electron acceptor is often selected such that the electron acceptor forms a solution that is colorless to the eye when the electron acceptor is dissolved in a suitable solvent such as an alcohol or in an ethylenically unsaturated monomer. A solution of the electron acceptor in an alcohol typically does not absorb in the visible region of the electromagnetic spectra. That is, the molar extinction coefficient of the electron acceptor can be less than 100 or less than 50 $l\text{-mole}^{-1}\text{cm}^{-1}$ at 350 nm.

Preferably, if used in the composition, the electron acceptor is present in an amount of at least 0.01 wt-%, and more preferably at least 0.10 wt-%, based on the total weight (including water) of the components of the hardenable composition. Preferably, the electron acceptor is present in an amount of no greater than 10 wt-%, and more preferably no greater than 5 wt-%, based on the total weight (including water) of the components of the hardenable composition.

The reducing agents (e.g., arylsulfinate salts and/or secondary reducing agents) or oxidizing agents of the present invention can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, e.g., with a photopolymerizable composition such as described U.S. Pat. No. 5,154,762 (Mitra et al.).

Sensitizers

The photopolymerizable compositions of the present invention can further include a sensitizing compound (i.e., sensitizer) as part of the initiator system. Electromagnetic radiation (e.g., actinic radiation) in the range of 250 to 1000 nanometers typically can be used to form an excited sensitizing compound. The sensitizing compound can be a ketone, a dye, a pigment, or combinations thereof.

Suitable sensitizing compounds include, but are not limited to, ketones (e.g., monoketones and diketones), coumarin dyes (e.g., ketocoumarins such as Coumarin 153), xanthene dyes (e.g., Rose Bengal and Rhodamine 6G), acridine dyes, thiazole dyes, thiazine dyes (e.g., Methylene Blue and Methylene Violet), oxazine dyes (e.g., Basic Blue 3 and Nile Blue Chloride), azine dyes (e.g., Methyl Orange), aminoketone dyes, porphyrins (e.g., porphyrazine), aromatic polycyclic hydrocarbons, p-substituted aminostyryl ketone compounds, aminotriaryl methanes, cyanine dyes (e.g., the cyanine dye described in *Biochemistry*, 12, 3315 (1974)), squarylium dyes, pyridinium dyes, benzopyrilium dyes, and triarylmethane (e.g., Malachite Green). In some applications, the sensitizing compounds include xanthenes, monoketones, diketones, or combinations thereof. Other suitable sensitizing dyes are described in F. J., Green, *The Sigma-Aldrich Handbook of Stains, Dyes, and Indicators*, Aldrich Chemical Company, Inc., Milwaukee, Wis. (1990). In some embodiments, the sensitizing compound is a xanthene dye such as fluorosceins, rhodamines, eosins, and pyronins.

Exemplary monoketones include 2,2-dihydroxybenzophenone, 4,4-dihydroxybenzophenone, and 2,4-dihydroxybenzophenone, di-2-pyridyl ketone, di-2-furanyl ketone, di-2-mercaptophenyl ketone, benzoin, fluorenone, chalcone, Michler's ketone, 2-fluoro-9-fluorenone, 2-chloromercaptoxanthone, acetophenone, benzophenone, 1- or 2-acetonaphthone, 9-acetylanthracene, 2-, 3-, or 9-acetylphenanthrene, 4-acetylbiphenyl, propiophenone, n-butyrophenone, valerophenone, 2-, 3-, or 4-acetylpyridine, 3-acetylcoumarin, and the like.

Exemplary diketones include aralkyldiketones such as anthraquinone, phenanthrenequinone, o-, m-, and p-diacetylbenzene, 1,3-, 1,4-, 1,5-, 1,6-, 1,7-, and 1-8 diacetylnaphthalene, 1,5-, 1,8-, and 9,10-diacetylanthracene, and the like. Exemplary alpha-diketones include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-, 3,3'-, and 4,4'-dihydroxybenzil, furil, di-3,3'-indolylethanedione, 2,3-bornanedione(camphorquinone), biacetyl, 1,2-cyclohexanedione, 3,3,6,6-tetramethylcyclohexanedione, 1,2-naphthaquinone, acenaphthaquinone, and the like. Additional diketones include 1-aryl-2-alkyl-1,2-ethanediones such as 1-phenyl-1,2-propanedione, as disclosed, for example, in U.S. Pat. No. 6,204,302 (Rawls et al.).

Additional ketocoumarins and p-substituted aminostyryl ketone compounds suitable as sensitizers are listed in Table II of U.S. Pat. No. 5,545,676 (Palazzotto).

The sensitizer can have a molar extinction coefficient up to 150,000 l-mole$^{-1}$cm$^{-1}$. In some applications, the sensitizer has a molar extinction coefficient that is up to 85,000 l-mole$^{-1}$cm$^{-1}$, up to 70,000, up to 50,000, up to 30,000, up to 10,000, or up to 5,000 l-mole$^{-1}$cm$^{-1}$.

For applications requiring deep cure (e.g., cure of highly filled dental composites), a sensitizing compound is typically selected that has an extinction coefficient less than 1000 l-mole$^{-1}$cm$^{-1}$. In other applications, the extinction coefficient at the wavelengths of light used for photopolymerization is less than 500 l-mole$^{-1}$cm$^{-1}$ or less than 100 l-mole$^{-1}$cm$^{-1}$. The alpha-diketones, for example, are sensitizing compounds that can be used for such applications. Alternatively, one can utilize dyes that exhibit a reduction in extinction coefficient, a reduction in light absorption, or photobleaching at the excitation wavelength upon light exposure.

The sensitizing compound can also be a pigment as described in U.S. Pat. No. 4,959,297 (Palazzotto et al.) and U.S. Pat. No. 4,257,915 (Eaton). Suitable inorganic pigments include, but are not limited to, titanium dioxide, strontium titanate, barium titanate, zinc oxide, zinc sulfide, zinc selenide, cadmium sulfide, cadmium selenide, cadmium telluride, or combinations thereof. Suitable organic pigments include, but are not limited to, phthalocyanine blue (pigment blue 15), copper polychlorophthalocyanine green (pigment green 7), copper polybromochlorophthalocyanine (pigment green 36), perylene scarlet (vat red 29), perylene vermillion (pigment red 23), perylene maroon, perylene Bordeaux, and perylene dianhydride (perylene red) as those described in "Pigments-Inorganic" and "Pigments-Organic" in *Kirk-Othmer Encyclopedia of Chemical Technology*, Third ed., Volume 17, pp. 788–817, John Wiley and Sons, New York, 1982. The organic pigments can also be semiconducting polymers as described by Y. M. Paushkin et al., *Organic Polymeric Semiconductors*, John Wiley & Sons, New York, 1974 and by J. M. Pearson, *Pure and Appl. Chem.*, 49, 463–477 (1977).

Preferred sensitizer compounds include camphorquinone, benzil, furil, 3,3,6,6-tetramethylcyclohexanedione, phenanthrenequinone, 1-phenyl-1,2-propanedione, and combinations thereof. A more preferred sensitizer compound is camphorquinone.

Preferably, if used in the composition, the sensitizer is present in an amount of at least 0.001 wt-%, and more preferably at least 0.01 wt-%, based on the total weight (including water) of the components of the hardenable composition. Preferably, the electron acceptor is present in an amount of no greater than 3.0 wt-%, and more preferably no greater than 1.0 wt-%, based on the total weight (including water) of the components of the hardenable composition.

Polymerizable Ethylenically Unsaturated Compounds

The compositions of the present invention include one or more polymerizable components thereby forming polymerizable (i.e., hardenable) compositions. The polymerizable components are typically ethylenically unsaturated compounds and may be monomers, oligomers, or polymers.

In certain embodiments, the compositions are photopolymerizable, i.e., the compositions contain a photopolymerizable component that is typically an ethylenically unsaturated compound and a photoinitiator (i.e., a photoinitiator system) that upon irradiation with actinic radiation initiates the polymerization (or hardening) of the composition. Such photopolymerizable compositions can be free radically polymerizable.

In certain embodiments, the compositions are chemically polymerizable, i.e., the compositions contain a chemically polymerizable component that is typically an ethylenically unsaturated compound and a chemical initiator (i.e., initiator system) that can polymerize, cure, or otherwise harden the composition without dependence on irradiation with actinic radiation. Such chemically polymerizable compositions are sometimes referred to as "self-cure" compositions and may include resin-modified glass ionomer cements, redox cure systems, and combinations thereof.

The ethylenically unsaturated compounds (i.e., compounds that contain at least one ethylenically-unsaturated double bond) of the present invention include monomers, oligomers, and polymers that can be polymerized using a free-radical polymerization reaction mechanism. Examples of ethylenically unsaturated compounds include (meth)acrylates (i.e., acrylates and methacrylates) including mono(meth)acrylates, di(meth)acrylates, poly(meth)acrylates, or combinations thereof. The compounds can be unsubstituted or substituted with a hydroxy. The compounds can contain acid functionality (as described in the following section) or be without acid functionality.

Exemplary ethylenically unsaturated compounds include methyl (meth)acrylate, ethyl(meth)acrylate, isopropyl(meth)acrylate, n-hexyl (meth)acrylate, stearyl(meth)acrylate, allyl (meth)acrylate, glycerol tri(meth)acrylate, ethyleneglycol di(meth)acrylate, diethyleneglycol di(meth)acrylate, triethyleneglycol di(meth)acrylate, 1,3-propanediol di(meth)acrylate, trimethylolpropane tri(meth)acrylate, 1,2,4-butanetriol tri(meth)acrylate, 1,4-cyclohexanediol di(meth)acrylate, pentaerythritol tetra(meth)acrylate, sorbitol hex(meth)acrylate, tetrahydrofurfuryl(meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate tri(meth)acrylate; (meth)acrylamides (i.e., acrylamides and methacrylamides) such as (meth)acrylamide, methylene bis-(meth)acrylamide, and diacetone (meth)acrylamide; urethane(meth)acrylates; the bis-(meth)acrylates of polyethylene glycols (preferably of molecular weight 200–500), copolymerizable mixtures of acrylated monomers such as those in U.S. Pat. No. 4,652,274 (Boettcher et al.), and acrylated oligomers such as those of U.S. Pat. No. 4,642,126 (Zador et al.); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The ethylenically unsaturated compound may also contain hydroxyl groups and free radically active functional groups in a single molecule. Examples of such materials include hydroxyalkyl(meth)acrylates, such as 2-hydroxyethyl(meth)acrylate and 2-hydroxypropyl(meth)acrylate; glycerol mono- and di-(meth)acrylate; trimethylolpropane mono- and di-(meth)acrylate; pentaerythritol mono-, di-, and tri-(meth)acrylate; sorbitol mono-, di-, tri-, tetra-, and penta-(meth)acrylate; and 2,2-bis[4-(2-hydroxy-3-methacryloxypropoxy)phenyl]propane (bisGMA). Suitable ethylenically unsaturated compounds are also available from a wide variety of commercial sources, such as Sigma-Aldrich, St. Louis, Mo. and Rhom and Tech, Inc., Darmstadt, Germany. Mixtures of ethylenically unsaturated compounds can be used if desired.

Preferred ethylenically unsaturated compounds for use in dental compositions include 2-hydroxyethyl methacrylate (HEMA), PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and NPGDMA (neopentylglycol dimethacrylate). Various combinations of the ethylenically unsaturated compounds can be used if desired.

Preferably, compositions of the present invention include at least 5% by weight, more preferably at least 10% by weight, and most preferably at least 15% by weight ethylenically unsaturated compounds, based on the total weight of the unfilled composition. Preferably, compositions of the present invention include at most 95% by weight, more preferably at most 90% by weight, and most preferably at most 80% by weight ethylenically unsaturated compounds, based on the total weight of the unfilled composition.

Polymerizable Ethylenically Unsaturated Compounds with Acid Functionality

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. Such ethylenically unsaturated compounds with acid functionality are present in certain embodiments of the present invention.

Exemplary ethylenically unsaturated compounds with acid functionality include, for example, α,β-unsaturated acidic compounds such as glycerol phosphate mono(meth)acrylates, glycerol phosphate di(meth)acrylates, hydroxyethyl(meth)acrylate phosphates, citric acid mono-, di-, and tri-(meth)acrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like. Certain preferred compositions of the present invention include an ethylenically unsaturated compound with acid functionality having at least one P—OH moiety.

Certain of these compounds are obtained, for example, as reaction products between isocyanatoalkyl(meth)acrylates and carboxylic acids (e.g., the bis-isocyanatoethylmethacrylate derivative of bis-hydroxymethylpropionic acid (PDMA) or the bis-isocyanatoethylmethacrylate derivative of citric acid (CDMA)). Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Provisional Application No. 60/437,106, filed Dec. 30, 2002; AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and European Pat. Application Publication Nos. EP 712,622 (Tokuyama Corp.) and EP 1,051,961 (Kuraray Co., Ltd.). Further, the combination of an ethylenically unsaturated phosphorylated compound and a carboxylic acid functional polymer are disclosed, for example, in U.S. Pat. No. 5,256,447 (Oxman et al.).

Preferably, when one or more ethylenically unsaturated compounds with acid functionality are present in the compositions of the present invention, the compositions include at least 1% by weight, more preferably at least 3% by weight, and most preferably at least 5% by weight ethylenically unsaturated compounds with acid functionality, based on the total weight of the unfilled composition. Preferably, compositions of the present invention include at most 80% by weight, more preferably at most 70% by weight, and most preferably at most 60% by weight ethylenically unsaturated compounds with acid functionality, based on the total weight of the unfilled composition.

Dental Additives

Certain embodiments of the present invention can include one or more dental additives. Exemplary dental additives include fluoride sources, whitening agents, anticaries agents (e.g., xylitol), remineralizing agents (e.g., calcium phosphate compounds), enzymes, breath fresheners, anesthetics, clotting agents, acid neutralizers, chemotherapeutic agents, immune response modifiers, medicaments, indicators, dyes, pigments, wetting agents, surfactants, buffering agents, viscosity modifiers, thixotropes, fillers, polyols, antimicrobial agents, antifungal agents, stabilizers, agents for treating xerostomia, desensitizers, and combinations thereof. Some of the above listed additives are described in more detail herein below.

Fluoride Sources

Suitable fluoride sources include fluoride salts as disclosed, for example, in U.S. Pat. No. 5,607,663 (Rozzi et al.), U.S. Pat. No. 5,662,887 (Rozzi et al.), U.S. Pat. No. 5,866,630 (Mitra et al.), U.S. Pat. No. 5,876,208 (Mitra et al.), U.S. Pat. No. 5,888,491 (Mitra et al.), and U.S. Pat. No. 6,312,668 (Mitra et al.). A preferred fluoride releasing source includes tetrafluoroborate anions as disclosed, for example, in U.S. Pat. No. 4,871,786 (Aasen et al.). A preferred repeating unit of a fluoride releasing source includes trimethylammoniumethyl methacrylate.

Fillers

The compositions of the present invention can contain fillers. Fillers may be selected from one or more of a wide variety of materials suitable for incorporation in compositions used for dental applications, such as fillers currently used in dental restorative compositions, and the like.

The filler is preferably finely divided. The filler can have a unimodial or polymodial (e.g., bimodal) particle size distribution. Preferably, the maximum particle size (the largest dimension of a particle, typically, the diameter) of the filler is less than 5 micrometers, more preferably less than 0.5 micrometers, and most preferably less than 0.1 micrometers. Preferably, the average particle size of the filler is less than 0.1 micrometers, and more preferably less than 0.075 micrometer.

The filler can be an inorganic material. It can also be a crosslinked organic material that is insoluble in the resin system, and is optionally filled with inorganic filler. The filler should in any event be nontoxic and suitable for use in the mouth. The filler can be radiopaque or radiolucent. The filler typically is substantially insoluble in water.

Examples of suitable inorganic fillers are naturally occurring or synthetic materials including, but not limited to: quartz; nitrides (e.g., silicon nitride); glasses derived from, for example, Zr, Sr, Ce, Sb, Sn, Ba, Zn, and Al; feldspar; borosilicate glass; kaolin; talc; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "1130," "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like.

Preferred non-acid-reactive filler particles are quartz, submicron silica, and non-vitreous microparticles of the type described in U.S. Pat. No. 4,503,169 (Randklev). Mixtures of these non-acid-reactive fillers are also contemplated, as well as combination fillers made from organic and inorganic materials.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like.

The filler can also be an acid-reactive filler. An acid-reactive filler is typically used in combination with an acid-functional resin component, and may or may not be used in combination with a non-reactive filler. The acid-reactive filler can, if desired, also possess the property of releasing fluoride. Suitable acid-reactive fillers include metal oxides, glasses, and metal salts. Preferred metal oxides include barium oxide, calcium oxide, magnesium oxide, and zinc oxide. Preferred glasses include borate glasses, phosphate glasses, and fluoroaluminosilicate ("FAS") glasses. FAS glasses are particularly preferred. The FAS glass preferably contains sufficient elutable cations so that a hardened dental composition will form when the glass is mixed with the components of the hardenable composition. The glass also preferably contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass preferably is in the form of particles that are sufficiently finely divided so that they can conveniently be mixed with the other cement components and will perform well when the resulting mixture is used in the mouth.

Preferably, the average particle size (typically, diameter) for the FAS glass is no greater than about 10 micrometers, and more preferably no greater than about 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT and KETAC-FIL (3M ESPE Dental Products, St. Paul, Minn.), FUJI II, GC FUJI LC and FUJI IX (G-C Dental Industrial Corp., Tokyo, Japan) and CHEMFIL Superior (Dentsply International, York, Pa.). Mixtures of fillers can be used if desired.

The FAS glass can optionally be subjected to a surface treatment. Suitable surface treatments include, but are not limited to, acid washing (e.g., treatment with a phosphoric acid), treatment with a phosphate, treatment with a chelating agent such as tartaric acid, and treatment with a silane or an acidic or basic silanol solution. Desirably the pH of the treating solution or the treated glass is adjusted to neutral or near-neutral, as this can increase storage stability of the hardenable composition.

In certain compositions mixtures of acid-reactive and non-acid-reactive fillers can be used in the hardenable compositions.

Other suitable fillers are disclosed in U.S. Pat. No. 6,387,981 (Zhang et al.) and U.S. Pat. No. 6,572,693 (Wu et al.) as well as International Publication Nos. WO 01/30306 (Windisch et al.), and WO 01/30307 (Zhang et al.). Filler components described in these documents include nano-sized silica particles and metal oxides, such as the oxides of yttrium, strontium, barium, zirconium, hafnium, niobium, tantalum, tungsten, bismuth, molybdenum, tin, zinc, lanthanide elements (i.e. elements having atomic numbers ranging from 57 to 71, inclusive), and cerium and combinations thereof.

For some embodiments of the present invention that include filler (e.g., dental adhesive compositions), the compositions preferably include at least 1% by weight, more preferably at least 2% by weight, and most preferably at least 5% by weight filler, based on the total weight of the composition. For such embodiments, compositions of the present invention preferably include at most 40% by weight, more preferably at most 20% by weight, and most preferably at most 15% by weight filler, based on the total weight of the composition.

For other embodiments (e.g., wherein the composition is a dental restorative or an orthodontic adhesive), compositions of the present invention preferably include at least 40% by weight, more preferably at least 45% by weight, and most preferably at least 50% by weight filler, based on the total weight of the composition. For such embodiments, compositions of the present invention preferably include at most 90% by weight, more preferably at most 80% by weight, even more preferably at most 70% by weight filler, and most preferably at most 50% by weight filler, based on the total weight of the composition.

Surfactants, Emulsifiers, and Water-in-Oil Emulsions

Surfactants can be utilized in some embodiments of the present invention, e.g., to aid in the preparation of dental compositions in the form of stable emulsions.

The emulsions preferably include at least 1% by weight water, more preferably, at least 3% by weight water, and most preferably, for certain embodiments, the emulsions include at least 5% by weight water, based on the total weight of the emulsion. They preferably include no more than 70% by weight water, and more preferably, no more than 50% by weight water, based on the total weight of the emulsion.

Typically emulsifiers and/or surfactants are used in the preparation of the emulsions of the present invention. The addition of low levels of stabilizing ingredients in the water phase can also be advantageous. Salts such as magnesium sulfate may be useful emulsion stabilizers. The addition of water-soluble gums such as guar derivatives, xanthan gum, and thickeners such as hydroxy ethyl cellulose, hydroxy propyl cellulose and carboxyl vinyl polymers may be helpful in stabilizing the emulsion.

A typical method for preparing water-in-oil macroemulsions includes heating, independently, the oil phase (containing the polymer and optional ingredients, e.g., surfactants) and the water phase (containing optional ingredients, e.g., surfactants and/or stabilizing ingredients), and slowly adding the water phase to the oil phase with good agitation. Homogenization is preferred, but may not be necessary. Upon cooling, other optional ingredients may be added, e.g., fillers. For the preparation of other water-in-oil macroemulsions, heating may not be necessary. Often the successful preparation of a macroemulsion depends on factors such as temperature, mixing rates and times, shear forces, etc.

Microemulsions can be oil-in-water (O/I) or water-in-oil (W/O) type, but the latter type is of particular interest in the present invention. Water-in-oil type microemulsions are formed under the conditions of dispersing water droplets having a size of at most 100 nanometers, typically obtained by the adsorption of a surfactant and a co-surfactant at the water/oil interface to lower the interfacial surface tension. The theory of microemulsions is available in the scientific literature including, for example, Leung et al, Chapter 9 in "Surfactants in Chemical Process Engineering," Marcel Dekker; Overbeek et al., "Surfactants" in *Microemulsions*, Academic Press (1984); Safran et al., *Phys. Rev. Lett.*, 50:1930 (1983); Ruckenstein et al., *J. Chem. Soc. Faraday Trans*, 2, 71:1690 (1975); and Ostrovsky et al., *J. Colloid. Interface Sci.*, 102:206 (1984).

In a typical procedure for making a water-in-oil microemulsion, the water is added slowly with mixing as a final step to the remaining components of the composition until initial turbidity is achieved. Often during this "titration" procedure the microemulsion forms spontaneously at the point of initial turbidity. This generally requires from 8 weight % to 12 weight % water based on the total weight of the composition. Typically, the microemulsion is formed by simple mixing and the oil and water-components of the composition do not need to be pre-mixed separately or heated prior to the addition of the water.

Photobleachable Dyes

In some embodiments, compositions of the present invention preferably have an initial color remarkably different than dental structures. Color is preferably imparted to the composition through the use of a photobleachable dye. The composition preferably includes at least 0.001% by weight photobleachable dye, and more preferably at least 0.002% by weight photobleachable dye, based on the total weight of the composition. The composition preferably includes at most 1% by weight photobleachable dye, and more preferably at most 0.1% by weight photobleachable dye, based on the total weight of the composition. The amount of photobleachable dye may vary depending on its extinction coefficient, the ability of the human eye to discern the initial color, and the desired color change.

The color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the composition and evaluating the change in color. Preferably, at least one photobleachable dye is at least partially soluble in a hardenable resin.

Exemplary classes of photobleachable dyes are disclosed, for example, in U.S. Pat. No. 6,331,080 (Cole et al.), U.S. Pat. No. 6,444,725 (Trom et al.), and U.S. Pat. No. 6,528,555 (Nikutowski et al.). Preferred dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

The color change in the inventive compositions is initiated by light. Preferably, the composition's color change is initiated using actinic radiation using, for example, a dental curing light which emits visible or near infrared (IR) light for a sufficient amount of time. The mechanism that initiates the color change in the compositions of the invention may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

The change in composition color from an initial color to a final color is preferably quantified by a Color Test as described below. Using the Color Test, a value of $\Delta E^*$ is determined, which indicates the total color change in a 3-dimensional color space. The human eye can detect a color change of approximately 3 $\Delta E^*$ units in normal lighting conditions. The dental compositions of the present invention are preferably capable of having a color change, $\Delta E^*$, of at least 20; more preferably, $\Delta E^*$ is at least 30; most preferably $\Delta E^*$ is at least 40.

Other Additives

Optionally, compositions of the present invention may contain diluents (e.g., water) and/or solvents (e.g., alcohols (e.g., propanol, ethanol), ketones (e.g., acetone, methyl ethyl ketone), and other non-hydroxylic solvents (e.g., dimethylformamide, dimethylacetamide, dimethylsulfoxide, 1-methyl-2-pyrrolidinone)). If desired, the compositions of the invention can contain other optional additives such as inhibitors, accelerators, and other ingredients that will be apparent to those skilled in the art.

Preparation and Use of the Dental Compositions

The polymerizable (i.e., hardenable) dental compositions of the present invention can be prepared by combining at least one ethylenically unsaturated compound, an arylsulfinate salt, optional electron acceptor, and optional sensitizer using conventional mixing techniques. The resulting composition may optionally contain a dental additive (e.g., filler, surfactant, bleachable dye), water, co-solvents, and other additives as described herein. In use, the compositions may contain a photoinitiator system (e.g., including an arylsulfinate salt electron donor, a sensitizer, and optionally an electron acceptor) and be hardened by photoinitiation, or may contain a thermal initiator system (e.g., including an arylsulfinate electron donor and an electron acceptor) and be hardened by chemical polymerization such as a redox cure mechanism. Alternatively, the hardenable composition may contain an initiator system (e.g., including an arylsulfinate salt electron donor, a sensitizer, and an electron acceptor) such that the composition can be both a photopolymerizable and a chemically polymerizable composition.

The polymerizable compositions of the invention can be supplied in a variety of forms including one-part systems and multi-part systems, e.g., two-part powder/liquid, paste/liquid, and paste/paste systems. Other forms employing multi-part combinations (i.e., combinations of two or more parts), each of which is in the form of a powder, liquid, gel, or paste are also possible. In a redox multi-part system, one part typically contains the electron accepter (e.g., an oxidizing agent) and another part typically contains the reducing agent (e.g., an arylsulfinate salt).

The components of the hardenable composition can be included in a kit, where the contents of the composition are packaged, as described below, to allow for storage of the components until they are needed.

When used as a dental composition, the components of the hardenable compositions can be mixed and clinically applied using conventional techniques. A curing light is generally required for the initiation of photopolymerizable compositions. The compositions can be in the form of composites or restoratives that adhere very well to dental structures. Optionally, a primer layer can be used on the dental structure on which the hardenable composition is used. The compositions, e.g., containing a FAS glass or other fluoride releasing material, can also provide very good long-term fluoride release. Some embodiments of the invention may provide resin modified glass ionomer cements or adhesives that can be cured in bulk without the application of light or other external curing energy, do not require a pre-treatment, have improved physical properties including improved flexural strength, and have high fluoride release for cariostatic effect.

The compositions of the invention are particularly well adapted for use in the form of a wide variety of dental materials, which may be filled or unfilled. They can be used in sealants or adhesives, which are typically lightly filled composites (up to 25 wt-% filler, based on the total weight of the composition) or unfilled compositions that are cured after being dispensed adjacent to a tooth (i.e., placing a dental material in temporary or permanent bonding or touching contact with a tooth). They can be used in cements, which are typically filled compositions (preferably containing greater than 25 wt-% filler, and more preferably greater than 40 wt-% filler; preferably containing up to 90 wt-% filler). They can also be used in restoratives, which include composites that are polymerized after being disposed adjacent to a tooth, such as filling materials. They can also be used in prostheses that are shaped and polymerized for final use (e.g., as a crown, bridge, veneer, inlay, onlay, or the like), before being disposed adjacent to a tooth.

The compositions have utility in clinical applications where cure of conventional light-curable cement may be difficult to achieve. Such applications include, but are not limited to, deep restorations, large crown or core build-ups, endodontic restorations, attachment of orthodontic brackets (including pre-coated brackets, where, for example, a paste portion could be pre-applied to the bracket and a liquid portion could later be brushed onto a tooth), bands, buccal tubes, and other devices, luting of metallic crowns or other light-impermeable prosthetic devices to teeth, and other restorative applications in inaccessible areas of the mouth.

Exemplary methods of using compositions of the present invention are described in the Examples. In some embodiments of the present invention, conditions effective to cause a composition (preferably, adhesive) to etch a dental structure surface include swishing the adhesive and/or adhesive/diluent mixture with a brush to mix/rubbing dental structure surface for a time effective to etch (i.e., for at least 3 seconds), typically for at least 5 seconds, often times for at least 10 seconds, and sometimes for at least 20 seconds.

Methods of bonding a dental material to a dental structure surface preferably result in a bond to enamel or dentin (or preferably both), of at least 7 MPa, more preferably at least 15 MPa, and most preferably at least 20 MPa.

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

Test Methods

Self-Curing Efficiency

A two-part "self-cure" test sample consisted of a Part A and Part B in the form of a resin or paste (i.e., filled paste). A portion (0.1 g) of Part A and a portion (0.1 g) of Part B were dispensed at room temperature onto a dental mixing pad in the form of two beads.

The two portions were mixed for 20 seconds with a spatula and immediately transferred to a 37° C. oven. The gel point of the resulting mixture was determined by running a ball applicator across the mixture at approximately every 30 seconds until the ball applicator would drag the mixture with itself and tear it, or when the 10-minute maximum test duration was reached.

Light-Curing Efficiency

A test sample (0.1 g) of resin or resin plus filler (i.e., filled paste), was dispensed out of a syringe onto a dental mixing pad in form of a bead. The test sample was irradiated with a XL 3000 halogen dental light (3M Company) for 40 seconds. Following irradiation, the sharp edge of a dental stainless steel spatula was used to indent the cured sample with an approximate force of 2 Kgf. The curing was judged "OK" when there was no indentation; "Brittle" when there was little or no indentation, but when the sample was brittle and broke into pieces; or "No Setting" when the sample stayed in a liquid or paste state. In Table 1, "YES" is the same as "OK" and "NO" is the same as "No Setting".

Storage Stability

Test samples were stored at 45° C. (approximately 30% relative humidity) and evaluated daily for 3 days and then weekly to determine the storage stability of the samples. A paste test sample (Part A or Part B of a two-part "self-cure", i.e., redox, composition) was determined to be stable at a given point in time if the sample remained in a non-hardened form and if a hardened composition was formed when the sample was mixed for 20 seconds with freshly prepared opposite paste (Part A or Part B of the two-part "self-cure" composition) at a weight ratio of Part A (having a reducing agent)/Part B (having an oxidizing agent)=3/1. The number of days that a test sample remained stable was reported.

Adhesion to Enamel or Dentin for "Light-Cure" Compositions

Adhesive strength to enamel or dentin for a given test sample was evaluated by the following procedure.

Preparation of Teeth. For each test sample, five bovine teeth of similar age and appearance were partially embedded in circular acrylic discs. The exposed portion of each tooth was ground flat and parallel to the acrylic disc using Grade 120 silicon carbide paper-backed abrasive mounted on a lapidary wheel, in order to expose the dentin or enamel. During this and subsequent grinding and polishing steps, the teeth were continuously rinsed with water. Further grinding and polishing of the teeth was carried out by mounting Grade 600 silicon carbide paper-backed abrasive on the lapidary wheel. The polished teeth were stored in deionized water and used for testing within 2 hours after polishing. The polished teeth were removed from the water and blotted dry.

Teeth Treatment. Previously made molds of 2-mm thick TEFLON sheeting with a 5-mm diameter hole punched through the sheeting were filled with Z100 composite samples (3M Company). The Z100 composite samples were exposed to radiation from a XL 3000 dental curing light for 60 seconds. The resulting hardened Z100 test buttons were removed from the molds and one side of each button was roughened with 320-grit sandpaper. In a controlled environment of 24° C. and 50% relative humidity and within one minute of preparing a test sample, a layer of the test sample was applied with a spatula to the roughened side of the Z100 button. The button with the applied test sample facing the tooth was pressed onto the tooth surface to create an assembly. The assembly was allowed to stand for an additional minute. Thereafter, the test sample layer was exposed to a XL 3000 dental curing light (3M Company) for 40 seconds. The entire assembly was placed in a humidity chamber set at 97% relative humidity and 37° C. for 15 minutes. The assembly was then placed into 37° C. deionized water for 24 hours.

Adhesive Bond Strength Testing. The adhesive strength of a cured test example was evaluated by mounting the assembly (described above) in a holder clamped in the jaws of an Instron™ (Instron 4505, Instron Corp. Canton, Mass.) with the polished tooth surface oriented parallel to the direction of pull. A loop of orthodontic wire (0.44-mm diameter) was placed around the Z100 button adjacent to the polished tooth surface. The ends of the orthodontic wire were clamped in the pulling jaw of the Instron apparatus and pulled at a crosshead speed of 2 mm/min, thereby placing the adhesive bond in shear stress. The force in kilograms (kg) at which the bond failed was recorded, and this number was converted to a force per unit area (units of $kg/cm^2$ or MPa) using the known surface area of the button. Each reported value of adhesion to enamel or adhesion to dentin represents the average of 5 replicates.

Compressive Strength (CS) of "Self-Cure" Compositions

In a controlled environment of 24° C. and 50% relative humidity, a "self-cure" (i.e., redox cure) composition was made by spatulating 3 g of paste A (having a reducing agent) with 1 g of paste B (having an oxidizing agent) for 25 seconds. Compressive strength samples were made by first injecting a mixed paste sample into a glass tube having a 4-mm inner diameter. The ends of the glass tube were plugged with silicone plugs. The filled tubes were subjected to 0.275 megapascal (MPa) pressure for 5 minutes. Thereafter, the tube was placed in a humidity chamber at 97% relative humidity and 37° C. for 20 minutes. From the humidity chamber, the tube was moved into 37° C. deionized water for 24 hours. Five such cured samples were cut to a length of 8 mm. Compressive strength was determined according to ISO Standard 7489 using an INSTRON universal tester (Instron Corp., Canton, Mass.) operated at a crosshead speed of 1 millimeter per minute (mm/min).

Compressive Strength (CS) of "Light-Cure" Compositions

A test sample was first injected into a glass tube having a 4-mm inner diameter. The ends of the glass tube were plugged with silicone plugs. The filled tubes were subjected to 0.275 megapascal (MPa) pressure for 5 minutes, irradiated with a XL 2500 curing light (3M Company) for 80 seconds, and placed in a KULZER UniXS (Kulzer, Inc., Germany) light box for 180 seconds. Five such cured samples were cut to a length of 8 mm and placed in 37° C. water for 1 day. Compressive strength was determined according to ISO Standard 7489 using an INSTRON universal tester (Instron Corp., Canton, Mass.) operated at a crosshead speed of 1 millimeter per minute (mm/min).

Diametral Tensile Strength (DTS) of "Self-Cure" and "Light-Cure" Compositions

Diametral tensile strength was measured using the above-described Compressive Strength Test Methods for "Self-Cure" or "Light-Cure" compositions, but using samples cut to a length of 2 mm. Results were reported as the average of 5 replicates.

| Abbreviations, Descriptions, and Sources of Materials | |
|---|---|
| Abbreviation | Description and Source of Material |
| BHT | 2,6-Di-tert-butyl-4-methylphenol (Sigma-Aldrich, St. Louis, MO) |
| Zr—Si | Silane-treated zirconia-silica (Zr—Si) filler prepared as described in U.S. Pat. No. 4,503,169 (Randklev) |
| FAS Glass | 50/50 blend of S/T (silane-treated) 4087 and S/T wet-milled 4087 fluoroaluminosilicate glass (both neutralized); prepared as described in pending patent; USPTO Ser. No. 10/121329; filed Apr. 12, 2003; Docket No. 57435US002 (Mitra et al.) |
| $TiO_2$ | Titanium dioxide (Degussa, Germany) |
| AEROSIL A200 | Fumed silica (Degussa) |
| CPQ | Camphorquinone (Sigma-Aldrich) |
| Cu(II)Ac | Copper(II) acetate monohydrate (Sigma-Aldrich) |
| DPIPF6 | Diphenyliodonium hexafluorophosphate, (Johnson Matthey, Alpha Aesar Division, Ward Hill, NJ) |
| NaP | Sodium persulfate (Sigma-Aldrich) |
| TEGDMA | Triethyleneglycol dimethacrylate (Sartomer, Exton, PA) |
| BisEMA6 | Ethoxylated bisphenol A dimethacrylate (Sartomer) |
| GDMA-P | Glycerol dimethacrylate phosphate; prepared as described in J. Dent. Res., 35, 8466 (1956)... cited in EP 0 237 233 (Oxman) (Also, see Example 3 in International Publication WO 02/092021 (Hecht et al.)) |
| HEMA-P | Mixture of mono-, di-, tri-HEMA phosphate and tetra-HEMA pyrophosphate (See Preparation Method described herein) |
| CBSA TBA | 4-Cyanobenzenesulfinic acid, tetrabutylammonium salt (See Preparation Method described herein) |
| CEBSA TBA | 4-Carboethoxybenzenesulfinic acid, tetrabutylammonium salt (See Preparation Method described herein) |
| EDMAB | Ethyl 4-(N,N-dimethylamino)benzoate (Sigma-Aldrich) |

Abbreviations, Descriptions, and Sources of Materials

| Abbreviation | Description and Source of Material |
|---|---|
| t-BDMA | 4-tert-Butyl dimethylaniline (Sigma-Aldrich) |
| DMAPE | 4-Dimethylaminophenethanol (Sigma-Aldrich) |
| DHEPT | Dihydroxyethyl p-toluidine (Gefachem-Prochemie, Leverkusen, Germany) |
| DMAEMA | 2-Dimethylaminoethyl methacrylate (Sigma-Aldrich) |
| TEA | Triethylamine (J. T. Baker, Phillipsburg, NJ) |
| DMA | N,N-Dimethylaniline (Sigma-Aldrich) |
| DMABN | N,N-Dimethylaminobenzonitrile (Sigma-Aldrich) |
| DMABA | 4-Dimethylaminobenzaldehyde (Sigma-Aldrich) |
| 4-DMAB | 4-Dimethylaminobenzoic acid (Alfa Aesar, Wardhill, MA) |
| 3-DMAB | 3-Dimethylaminobenzoic acid (Lancaster Synthesis Ltd., Windham, NH) |
| 4-DMABn | 4-Dimethylaminobenzoin (Sigma-Aldrich) |
| N-PhG | N-phenylglycine (Sigma-Aldrich) |
| N-PhGEE | N-phenylglycine ethyl ester (Eastman Kodak, Rochester, NY) |

Starting Materials Preparations

Preparation of Arylsulfinate Salts

4-Cyanobenzenesulfinic acid, tetrabutylammonium salt (CBSA TBA) and 4-Carboethoxybenzenesulfinic acid, tetrabutylammonium salt (CEBSA TBA) were prepared by methods similar to those disclosed, for example, in Assignee's U.S. patent application Ser. No. 10/672,762, filed Sep. 26, 2003 (now U.S. Pat. No. 7,030,169 (Kalgutkar et al.)).

In brief, each tetrabutylammonium benzenesulfinate was prepared from the corresponding alkali metal benzenesulfinate by extracting the corresponding benzenesulfinic acid from an acidic, aqueous solution of the alkali metal benzenesulfinate with ethyl acetate. The organic phase was evaporated to dryness and the resultant solid was dissolved in 50% (v/v) aqueous methanol. This solution was then titrated with an aqueous solution of tetrabutylammonium hydroxide. The mixture was evaporated to dryness to afford the tetrabutylammonium benzenesulfinate as a yellow oil.

Each alkali metal benzenesulfinate was, in turn, prepared by hydrolysis of the corresponding benzenesulfonyl chloride to form the corresponding benzenesulfinic acid as a colorless solid. An aqueous methanol solution of the benzenesulfinic acid was neutralized with an alkali metal hydroxide to afford the alkali metal benzenesulfinate salt.

Preparation of HEMA-P (Mixture of HEMA Phosphates and Tetra-HEMA Pyrophosphate)

A 1-liter three-necked round-bottomed flask fitted with a reflux condenser with gas inlet, a mechanical stirrer, and an addition funnel with gas outlet was charged with 76.7 g of POCl$_3$ and 500 ml THF. A solution of 130.5 g HEMA, 101.5 g triethylamine (TMA) and 87 g of THF was placed in the addition funnel. The flask was cooled via an ice-water-salt bath to approximately −5° C. The solution was added dropwise with stirring over a period of 25 minutes during which the temperature was maintained between 0° C. and −5° C. The mixture was stirred for three hours allowing the temperature to rise to room temperature. To the flask was added an additional 200 ml of THF to facilitate stirring. To the addition funnel was added a solution of 51 g of TEA and 6.8 g water in 50 ml of THF. After cooling the flask to 0–5° C. via the ice-water-salt bath, the solution was added dropwise during 16 minutes. The mixture was allowed to come to room temperature and stirred for 18 hours. The mixture was filtered to remove the precipitated salts and the THF removed in vaccuo. The product, 168 g, was a light orange liquid which was characterized by $^1$H, $^{13}$C and $^{31}$P NMR to be a mixture of mono-, di-, and tri-HEMA phosphate and tetra-HEMA pyrophosphate.

Examples 1–4

Evaluation of Various Electron Donors in Initiator Systems (Light-Cure Mode)

Resin A was prepared by combining TEGDMA (24.85 parts), BisEMA6 (24.85 parts), HEMA-P (49.70 parts), CPQ (0.30 parts), and BHT (0.30 parts) to afford a homogeneous composition.

Various electron donor compounds were combined with Resin A and the resulting compositions evaluated for curing according to the Light-Curing Efficiency Test Method described herein. The electron donor compounds, their concentration and solubility observations in Resin A, and the light-curing results are provided in Table 1. The studies were repeated with DPIPF6 (1 part) added to the compositions and the curing results were essential identical to the results without added DPIPF6. The mixture of Resin A with CBSA TBA at 3% and at 10% and with CEBSA TBA at 3% and at 10% were designated Examples 1, 2, 3, and 4, respectively.

It is noted that the light curing efficiency of Resin A plus an aryl sulfinate tetrabutylammonium salt (either CBSA TBA or CEBSA TBA) was dependent upon the concentration of the sulfinate salt in the resin.

TABLE 1

Light-Curing Results of Resin A Containing Various Electron Donor Compounds

| Electron Donor Compound | Physical State of Compound | Compound Concentration in Resin A (Wt. %) | Solubility/ Miscibility Observations | Curing Result |
|---|---|---|---|---|
| DMAPE | Solid | 2% | Dissolved | NO |
| DHEPT | Solid | 2% | Dissolved | NO |
| EDMAB | Solid | 2% | Dissolved | YES |
| 4-DMAB | Solid | 2% | Not totally soluble | Brittle |
| t-BDMA | Liquid | 2% | Miscible | NO |
| DMA | Liquid | 2% | Miscible | YES |
| DMABN | Solid | 2% | Dissolved | YES |
| DMABA | Solid | 2% | Dissolved | Brittle |
| 3-DMAB | Solid | 2% | Not totally soluble | NO |
| 4-DMABn | Solid | 2% | Not totally soluble | NO |
| N-PhG | Solid | 2% | Not totally soluble | NO |
| N-PhGEE | Solid | 2% | Dissolved | Brittle |
| DMAEMA | Liquid | 2% | Miscible | NO |
| TEA | Liquid | 2% | Miscible | NO |
| CBSA TBA (Example 1) | Liquid | 3% | Miscible | Brittle |
| CBSA TBA (Example 2) | Liquid | 10% | Miscible | YES |
| CEBSA TBA (Example 3) | Wax | 3% | Dissolved | NO |
| CEBSA TBA (Example 4) | Wax | 10% | Dissolved | Brittle |

Examples 5–6

Evaluation of Aryl Sulfinate Salts as Electron Donors in Initiator Systems (Self-Cure and Light-Cure Modes)

Examples 5 and 6 were "self-adhesive" compositions made from two-part paste/paste components. Paste A1 and Paste A2 (each containing polymerizable components, EDMAB and CBSA TBA electron donors, and fillers) were prepared by combining the components in the concentrations shown in Table 2. Paste B (containing acidic and non-acidic polymerizable components, CPQ sensitizer, Cu(II) Ac and NaP oxidizing agents (i.e., electron acceptors), and fillers) was prepared by combining the components in the concentrations shown in Table 3.

TABLE 2

| Component (Parts by Weight) | Paste A1 | Paste A2 |
|---|---|---|
| TEGDMA | 12.9 | 12.9 |
| BisEMA6 | 7.7 | 7.7 |
| BHT | 0.04 | 0.04 |
| EDMAB | 2.6 | 2.6 |
| FAS Glass | 73.4 | 73.6 |
| $TiO_2$ | 0.5 | 0.5 |
| AEROSIL A200 | 2.3 | 2.3 |
| CBSA TBA | 0.6 | 0 |
| CEBSA TBA | 0 | 0.4 |
| Total: | 100 | 100 |

TABLE 3

| Component (Parts by Weight) | Paste B |
|---|---|
| TEGDMA | 4.3 |
| BisEMA6 | 2.6 |
| GDMA-P | 47.2 |
| BHT | 0.11 |
| CPQ | 0.2 |
| Cu(II)Ac | 0.1 |
| NaP | 6.9 |
| Zr-Si Filler | 34.3 |
| AEROSIL A200 | 4.3 |
| Total: | 100 |

Example 5 was prepared by spatulating 3 g of Paste A1 with 1 g of Paste B for 20 seconds. Example 6 was prepared by spatulating 3 g of Paste A2 with 1 g of Paste B for 20 seconds. Examples 5 and 6 were evaluated in the "Self-Cure" mode (i.e., without subjecting to an external dental curing light) for Compression Strength (CS) and Diametral Tensile Strength (DTS), according to the "Self-Cure" Test Methods described herein. Example 5 was also evaluated in the "Light-Cure" mode (i.e., with exposure to an external dental curing light) for Compression Strength (CS), Diametral Tensile Strength (DTS), and Adhesion to Enamel and Dentin according to the "Light-Cure" Test Methods described herein. Test results are provided in Table 4 with Standard Deviations indicated in parentheses.

TABLE 4

| Test Method | Example 5 | Example 6 |
|---|---|---|
| "Self-Cure" CS (MPa) | 278 (26) | 300 (11) |
| "Self-Cure" DTS (MPa) | 45 (1) | 47 (4) |
| "Light-Cure" CS (MPa) | 257 (34) | NT* |
| "Light-Cure" DTS (MPa) | 44 (1) | NT |
| "Light-Cure" Adhesion to Enamel (MPa) | 12.9 (3.7) | NT |
| "Light-Cure" Adhesion to Dentin (MPa) | 15.5 (5.7) | NT |

*NT - Not Tested

Storage Stability Evaluations

Utilizing the Storage Stability Test Method described herein, Paste A1 was found to be stable for more than 80 days at 45° C. and more than 9 months at room temperature (23° C.); Paste A2 was found to be stable for about 2 weeks at 45° C. Paste B was used in the test method.

Examples 7–8

Evaluation of Aryl Sulfinate Salts as Electron Donors in Initiator Systems (Self-Cure Mode)

Resin B was prepared by combining TEGDMA (62.31 parts), BisEMA6 (37.38 parts), and BHT (0.31 parts) to afford a homogeneous composition.

Paste C was prepared by combining TEGDMA (6.65 parts), BisEMA6 (3.99 parts), BHT (0.10 parts), CPQ (0.32 parts), GDMA-P (73.15 parts), Cu(II)Ac (0.16 parts), NaP (10.64 parts), and AEROSIL A200 (5.32 parts) to afford a homogeneous composition.

Various electron donor compounds were combined with Resin B and the resulting mixtures were combined with Paste C in 1:1 weight ratios. The resulting compositions were evaluated for curing according to the Self-Curing Efficiency Test Method described herein. The electron donor compounds, their concentrations and solubility observations in Resin B, and the self-curing results are provided in Table 5. The composition of Resin B with 5% CBSA TBA combined with Paste C was designated Example 7 and the composition of Resin B with 5% CEBSA TBA combined with Paste C was designated Example 8.

TABLE 5

Self-Curing Results of Compositions Containing Various Electron Donor Compounds

| Electron Donor Compound | Physical State of Compound | Compound Concentration in Resin B (Wt. %) | Solubility/ Miscibility Observations | Gel Time (Minutes: Seconds) |
|---|---|---|---|---|
| None | — | — | — | >10:00 (No Setting) |
| EDMAB | Solid | 5% | Dissolved | >10:00 (No Setting) |
| CBSA TBA (Example 7) | Liquid | 5% | Miscible | <0:30 |
| CEBSA TBA (Example 8) | Wax | 5% | Dissolved | 2:30 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A polymerizable dental composition suitable for use in the oral environment comprising:
    an ethylenically unsaturated compound;
    a dental additive; and
    an initiator system comprising an arylsulfinate salt having an anion of Formula I

    I and a cation selected from:
    1) a phosphorus-containing cation of Formula III:

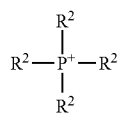    III where each $R^2$ is independently an unsubstituted alkyl, an alkyl substituted with a hydroxy, an unsubstituted aryl, an aryl substituted with an alkyl, hydroxy, or combinations thereof; or
    2) a nitrogen-containing cation having a ring structure comprising a 4 to 12 member heterocyclic group having a positively charged nitrogen atom, said heterocyclic being saturated or unsaturated and having up to 3 heteroatoms selected from oxygen, sulfur, nitrogen, or combinations thereof, wherein said ring structure is unsubstituted or substituted with a substituent selected from an alkyl, aryl, acyl, alkoxy, aryloxy, halo, mercapto, amino, hydroxy, azo, cyano, carboxy, alkoxycarbonyl, aryloxycarbonyl, halocarbonyl, or combinations thereof,
    wherein the arylsulfinate salt has an oxidation potential in N,N-dimethylformamide of 0.0 to +0.4 volts versus a silver/silver nitrate reference electrode, and wherein $Ar^1$ is a $C_{6-30}$ aryl or a $C_{3-30}$ heteroaryl that is unsubstituted or substituted with an electron withdrawing group or an electron withdrawing group in combination with an electron donating group.

2. The polymerizable dental composition of claim 1 wherein the dental additive is selected from the group consisting of fluoride sources, whitening agents, anticaries agents, remineralizing, enzymes, breath fresheners, anesthetics, clotting agents, acid neutralizers, chemotherapeutic agents, immune response modifiers, medicaments, indicators, dyes, pigments, wetting agents, surfactants, buffering agents, viscosity modifiers, thixotropes, fillers, polyols, antimicrobial agents, antifungal agents, stabilizers, agents for treating xerostomia, desensitizers, and combinations thereof.

3. The polymerizable dental composition of claim 1 wherein the dental additive is a photobleachable dye.

4. The polymerizable dental composition of claim 1 wherein the composition is in a form selected from the group consisting of a dispersion, a suspension, an emulsion, a solution, and combinations thereof.

5. The polymerizable dental composition of claim 1 wherein the composition is a primer, a dental adhesive, an orthodontic adhesive, a coating, a sealant, a cement, a restorative, or combinations thereof.

6. The polymerizable dental composition of claim 1 wherein the initiator system further comprises a sensitizer capable of absorbing a wavelength of actinic radiation in the range of 250 to 1000 nanometers.

7. The polymerizable dental composition of claim 6 wherein the sensitizer is selected from the group consisting of camphorquinone, benzil, furil, 3,3,6,6-tetramethylcyclohexanedione, phenanthraquinone, 1-phenyl-1,2-propanedione, and combinations thereof.

8. The polymerizable dental composition of claim 1 wherein the initiator system further comprises an electron acceptor having a reduction potential in N,N-dimethylformamide of +0.4 to −1.0 volts versus a silver/silver nitrate reference electrode.

9. The polymerizable dental composition of claim 8 wherein the electron acceptor is an iodonium salt, a hexaarylbisimidizole, a persulfate, a peroxide, a metal ion in an oxidized state, or combinations thereof.

10. The polymerizable dental composition of claim 8 wherein the initiator system further comprises a sensitizer capable of absorbing a wavelength of actinic radiation in the range of 250 to 1000 nanometers.

11. The polymerizable dental composition of claim 1 wherein the initiator system further comprises a reducing agent different from the arylsulfinate salt.

12. A polymerizable composition comprising:
    an ethylenically unsaturated compound; and
    an initiator system comprising an arylsulfinate salt having an anion of Formula I

    I and a cation selected from:
    1) a phosphorus-containing cation of Formula III:

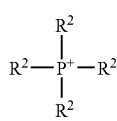    III where each $R^2$ is independently an unsubstituted alkyl, an alkyl substituted with a hydroxy, an unsubstituted aryl, an aryl substituted with an alkyl, hydroxy, or combinations thereof; or
    2) a nitrogen-containing cation having a ring structure comprising a 4 to 12 member heterocyclic group having a positively charged nitrogen atom, said heterocyclic being saturated or unsaturated and having up to 3 heteroatoms selected from oxygen, sulfur, nitrogen, or combinations thereof, wherein said ring structure is unsubstituted or substituted with a substituent selected from an alkyl, aryl, acyl, alkoxy, aryloxy, halo, mercapto, amino, hydroxy, azo, cyano, carboxy, alkoxycarbonyl, aryloxycarbonyl, halocarbonyl, or combinations thereof,
    wherein the arylsulfinate salt has an oxidation potential in N,N-dimethylformamide of 0.0 to +0.4 volts versus a silver/silver nitrate reference electrode, and wherein $Ar^1$ is a $C_{6-30}$ aryl or a $C_{3-30}$ heteroaryl that is unsubstituted or substituted with an electron withdrawing group or an electron withdrawing group in combination with an electron donating group, and
    wherein the polymerizable composition is a dental material suitable for use in the oral environment.

13. The polymerizable composition of claim 12 wherein the initiator system further comprises a sensitizer capable of absorbing a wavelength of actinic radiation in the range of 250 to 1000 nanometers.

14. The polymerizable composition of claim 12 wherein the initiator system further comprises an electron acceptor having a reduction potential in N,N-dimethylformamide of +0.4 to −1.0 volts versus a silver/silver nitrate reference electrode.

15. The polymerizable composition of claim 14 wherein the initiator system further comprises a sensitizer capable of absorbing a wavelength of actinic radiation in the range of 250 to 1000 nanometers.

16. The polymerizable composition of claim 12 wherein the initiator system further comprises a reducing agent different from the arylsulfinate salt.

17. The polymerizable composition of claim 12 further comprising a photobleachable dye.

18. The polymerizable dental composition of claim 2 wherein the anticaries agent comprises xylitol.

19. The polymerizable dental composition of claim 2 wherein the remineralizing agent comprises a calcium phosphate compound.

20. A polymerizable dental composition suitable for use in the oral environment comprising:
an ethylenically unsaturated compound;
a dental additive; and
an initiator system comprising an arylsulfinate salt having an anion of Formula I

and a cation of Formula II:

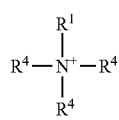

where $R^1$ and each $R^4$ are independently alkyl groups having at least 3 carbon atoms, and wherein the arylsulfinate salt has an oxidation potential in N,N-dimethylformamide of 0.0 to +0.4 volts versus a silver/silver nitrate reference electrode, and wherein $Ar^1$ is a $C_{6-30}$ aryl or a $C_{3-30}$ heteroaryl that is unsubstituted or substituted with an electron withdrawing group or an electron withdrawing group in combination with an electron donating group.

21. A polymerizable composition comprising:
an ethylenically unsaturated compound; and
an initiator system comprising an arylsulfinate salt having an anion of Formula I

and a cation of Formula II:

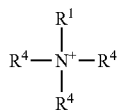

where $R^1$ and each $R^4$ are independently alkyl groups having at least 3 carbon atoms, and wherein the arylsulfinate salt has an oxidation potential in N,N-dimethylformamide of 0.0 to +0.4 volts versus a silver/silver nitrate reference electrode, and wherein $Ar^1$ is a $C_{6-30}$ aryl or a $C_{3-30}$ heteroaryl that is unsubstituted or substituted with an electron withdrawing group or an electron withdrawing group in combination with an electron donating group, and wherein the polymerizable composition is a dental material suitable for use in the oral environment.

* * * * *

UNITED STATES PATENT AND TRADEMARK OFFICE
CERTIFICATE OF CORRECTION

PATENT NO.       : 7,250,452 B2
APPLICATION NO.  : 10/672814
DATED            : July 31, 2007
INVENTOR(S)      : Afshin Falsafi It is certified that error appears in the above-identified patent and that said Letters Patent is hereby corrected as shown below:

Column 6
Line 60, delete "therof." and insert -- thereof. --, therefor.

Column 12
Lines 36-37, delete "tetraalkyammonium" and insert -- tetraalkylammonium --, therefor.

Column 13
Line 5, delete "i.e" and insert -- i.e., --, therefor.

Column 21
Line 33, delete ""1130,"" and insert -- "130," --, therefor.

Column 33
Line 51, in Claim 2, delete "remineralizing," and insert -- remineralizing agents, --, therefor.

Column 34
Line 48, in Claim 12, delete "heterocyclie" and insert -- heterocyclic --, therefor.

Column 35
Line 30, in Claim 20, delete " $Ar^1-SO_2^+$ " and insert -- $Ar^1-SO_2^{\cdot-}$ --, therefor.

UNITED STATES PATENT AND TRADEMARK OFFICE
CERTIFICATE OF CORRECTION

PATENT NO. : 7,250,452 B2
APPLICATION NO. : 10/672814
DATED : July 31, 2007
INVENTOR(S) : Afshin Falsafi It is certified that error appears in the above-identified patent and that said Letters Patent is hereby corrected as shown below:

Column 36
Line 16, in Claim 21, delete " $Ar^1—SO_2^+$ " and insert -- $Ar^1—SO_2^·$ --, therefor.

Signed and Sealed this

Tenth Day of June, 2008

JON W. DUDAS
*Director of the United States Patent and Trademark Office*